United States Patent
Hu et al.

(10) Patent No.: US 9,469,868 B2
(45) Date of Patent: Oct. 18, 2016

(54) METHODS AND COMPOSITIONS IN PARTICLE-BASED DETECTION OF TARGET MOLECULES USING COVALENT BOND FORMING REACTIVE PAIRS

(75) Inventors: Celine Hu, Tiburon, CA (US); Hetian Gao, Fremont, CA (US); Julie Perkins, Sunnyvale, CA (US)

(73) Assignee: Headway Technologies, Inc., Milpitas, CA (US)

( * ) Notice: Subject to any disclaimer, the term of this patent is extended or adjusted under 35 U.S.C. 154(b) by 729 days.

(21) Appl. No.: 12/612,432

(22) Filed: Nov. 4, 2009

(65) Prior Publication Data

US 2010/0130383 A1    May 27, 2010

Related U.S. Application Data

(60) Provisional application No. 61/115,401, filed on Nov. 17, 2008.

(51) Int. Cl.
| | | |
|---|---|---|
| *C12Q 1/68* | (2006.01) | |
| *G01N 27/74* | (2006.01) | |
| *G01N 33/58* | (2006.01) | |

(52) U.S. Cl.
CPC ............ *C12Q 1/682* (2013.01); *C12Q 1/6834* (2013.01); *C12Q 1/6837* (2013.01); *G01N 27/745* (2013.01); *C12Q 2537/125* (2013.01); *C12Q 2563/143* (2013.01); *C12Q 2563/149* (2013.01); *G01N 33/582* (2013.01)

(58) Field of Classification Search
CPC .. C12Q 1/682; C12Q 1/6837; C12Q 1/6834; C12Q 2563/143; C12Q 2563/125; G01N 27/745; G01N 33/582
See application file for complete search history.

(56) References Cited

U.S. PATENT DOCUMENTS

| | | |
|---|---|---|
| 4,599,303 A | 7/1986 | Yabusaki et al. |
| 4,826,967 A | 5/1989 | Glass |
| 5,028,594 A | 7/1991 | Carson |
| 5,082,934 A | 1/1992 | Saba et al. |
| 5,124,246 A | 6/1992 | Urdea et al. |
| 5,196,306 A | 3/1993 | Bobrow et al. |
| 5,512,439 A | 4/1996 | Hornes et al. |

(Continued)

FOREIGN PATENT DOCUMENTS

| | | |
|---|---|---|
| JP | 2007-189991 A | 8/2007 |
| JP | 2007-225586 | 9/2007 |

(Continued)

OTHER PUBLICATIONS

Gramlich et al. (Angew. Chem. Int. Ed., 2008, 47:8350-8358).*

(Continued)

*Primary Examiner* — Jeremy C Flinders
(74) *Attorney, Agent, or Firm* — Michael B. Rubin; Bozicevic, Field & Francis LLP

(57) ABSTRACT

Methods and compositions which can be used to increase the strength and/or probability of forming a binding complex comprising a target molecule and a substrate are disclosed. In one aspect, linking molecules having one or more members of a reactive pair are disclosed which can be used to increase the number of intra-complex binding interactions in a complex comprising a target molecule and a substrate. Intra-complex crosslinking and inter-complex crosslinking can be utilized in connection with these methods and compositions to further strengthen and stabilize the disclosed binding complexes.

17 Claims, 17 Drawing Sheets

X (1st member of reactive pair)
Y (2nd member of reactive pair)

(56) References Cited

U.S. PATENT DOCUMENTS

| | | | |
|---|---|---|---|
| 5,580,731 | A | 12/1996 | Chang et al. |
| 5,616,464 | A | 4/1997 | Albagli et al. |
| 5,635,352 | A | 6/1997 | Urdea et al. |
| 5,653,859 | A | 8/1997 | Parton et al. |
| 5,767,259 | A | 6/1998 | Albagli et al. |
| 5,981,297 | A | 11/1999 | Baselt |
| 6,004,513 | A | 12/1999 | Albagli et al. |
| 6,005,093 | A | 12/1999 | Wood et al. |
| 6,177,243 | B1 | 1/2001 | Albagli et al. |
| 6,187,532 | B1 | 2/2001 | Wood et al. |
| 6,277,570 | B1 | 8/2001 | Wood et al. |
| 6,303,799 | B1 | 10/2001 | Cheng et al. |
| 6,495,676 | B1 | 12/2002 | Wood et al. |
| 6,573,048 | B1 | 6/2003 | VanAtta et al. |
| 6,590,091 | B2 | 7/2003 | Albagli et al. |
| 6,696,246 | B1 * | 2/2004 | Huan et al. .................. 506/9 |
| 6,737,239 | B2 | 5/2004 | Wood et al. |
| 6,743,639 | B1 | 6/2004 | Tondra et al. |
| 6,800,768 | B1 | 10/2004 | Cheng et al. |
| 6,875,621 | B2 | 4/2005 | Tondra |
| 7,033,758 | B2 | 4/2006 | Kenny et al. |
| 7,163,788 | B2 | 1/2007 | Tong |
| 7,223,833 | B1 | 5/2007 | Nielsen et al. |
| 7,332,355 | B2 | 2/2008 | Hsieh-Wilson et al. |
| 2001/0012616 | A1 | 8/2001 | Wood et al. |
| 2002/0051971 | A1 | 5/2002 | Stuelpnagel et al. |
| 2002/0102578 | A1 | 8/2002 | Dickinson et al. |
| 2002/0127574 | A1 | 9/2002 | Mirkin et al. |
| 2002/0177157 | A1 | 11/2002 | Luo et al. |
| 2003/0148282 | A1 * | 8/2003 | Mirkin et al. .................. 435/6 |
| 2003/0166177 | A1 | 9/2003 | Dordick et al. |
| 2005/0100930 | A1 | 5/2005 | Wang et al. |
| 2006/0177850 | A1 | 8/2006 | Schermer et al. |
| 2006/0252085 | A1 | 11/2006 | Pollner et al. |
| 2006/0286583 | A1 | 12/2006 | Luo et al. |
| 2007/0117151 | A1 | 5/2007 | Frederix et al. |
| 2007/0184436 | A1 | 8/2007 | Myerson et al. |
| 2007/0202576 | A1 | 8/2007 | Bodepudi et al. |
| 2008/0038725 | A1 | 2/2008 | Luo et al. |
| 2008/0220979 | A1 | 9/2008 | Wang et al. |
| 2009/0048123 | A1 | 2/2009 | Medintz et al. |
| 2009/0104707 | A1 | 4/2009 | Wang et al. |
| 2009/0111709 | A1 | 4/2009 | Burke et al. |
| 2010/0129819 | A1 | 5/2010 | Hu et al. |
| 2011/0059444 | A1 | 3/2011 | Stromberg et al. |
| 2012/0289419 | A1 | 11/2012 | Hu et al. |

FOREIGN PATENT DOCUMENTS

| | | |
|---|---|---|
| WO | 90/11523 | 10/1990 |
| WO | 95/16055 A1 | 6/1995 |
| WO | 97/27317 A1 | 7/1997 |
| WO | 03/083440 A2 | 10/2003 |
| WO | 03083440 | 10/2003 |
| WO | WO 03083440 | 10/2003 |
| WO | 2005/033343 A2 | 4/2005 |
| WO | 2006124771 | 11/2006 |
| WO | WO2007005626 | 1/2007 |
| WO | WO 2007056250 A2 * | 5/2007 |
| WO | 2008/052775 | 5/2008 |
| WO | WO2008101024 | 8/2008 |
| WO | WO 2009112498 | 9/2009 |

OTHER PUBLICATIONS

Invitrogen (Dynabeads M-280, Oct. 2011).*
Kocalka et al. (ChemBiochem, 2008, 9:1280-1285).*
Park, et al., Array-Based Electrical Detection of DNA with Nanoparticle Probes, Science Feb. 22, 2002: vol. 295. No. 5559, pp. 1503-1506.
Baselt et al., A biosensor based on magnetoresistance technology. Biosens. Bioelectron. 1998;13(7-8):731-9.
Baskin et al., Copper-free click chemistry for dynamic in vivo imaging. Proc. Natl. Acad. Sci. USA 2007;104 (43):16793-7.
Bird et al., Single-chain antigen-binding proteins. Science 1988;242:423-6.
Casey, 2005 Nobel Prize in Chemistry: Development of the olefin metathesis method in organic synthesis. J. Chem. Edu. 2006;83(2):192-5.
Chan et al., Polytriazoles as copper(I)-stabilizing ligands in catalysis. Org. Lett. 2004;6(17):2853-5.
Chavali et al., Oligonucleotide properties determination and primer designing: a critical examination of predictions. Bioinformatics 2005;21(20):3918-25.
Donnelly et al., 'Click' cycloaddition catalysts: copper(I) and copper(II) tris(triazolylmethyl)amine complexes. Chem. Commun. 2008:2459-61.
Drake et al., Gd-doped iron-oxide nanoparticles for tumour therapy via magnetic field hyperthermia. J. Mater. Chem. 2007;17:4914-8.
Ebright et al., Conversion of a helix-turn-helix motif sequence-specific DNA binding protein into a site-specfic DNA cleavage agent. Proc. Natl. Acad. Sci. USA 1990;87:2882-6.
Edelstein et al., The BARC biosensor applied to the detection of biological warfare agents. Biosens. Bioelectron. 2000;14:pp. 805-813.
Ferreira et al., Biodetection using magnetically labeled biomolecules and arrays of spin valve sensors (invited). J. Appl. Phys. 2003;93(10):7281-6.
Ferreira et al., Effect of spin-valve sensor magnetostatic fields on nanobead detection for biochip applications. J Appl. Phys. 2005;97(10Q904):1-3.
Graham et al., Single magnetic microsphere placement and detection on-chip using current line designs with integrated spin valve sensors: Biotechnological applications. J. Appl. Phys. 2002;91(10):7786-8.
He et al., Empirical establishment of oligonucleotide probe design criteria. Appl. Env. Microbiol. 2005;71(7):3753-60.
Himo et al., Copper(I)-catalyzed synthesis of azoles. DFT study predicts unprecedented reactivity with intermediates. J. Amer. Chem. Soc. 2005;127:210-6.
Hunkapiller et al., The growing immunoglobulin gene superfamily. Nature 1986;323:15-6.
Huston et al., Protein engineering of antibody binding sites: Recovery of specific activity in an anti-digoxin single-chain Fv analogue produced in *Escherichia coli*. Proc. Natl. Acad. Sci. USA 1988;85:5879-83.
Ito et al., Development of an artificial antibody system with multiple valency using an Fv fragment fused to a fragment of protein A. J. Biol. Chem. 1993;268(27):20668-75.
Kim et al., Site-specific gene modification by PNAs conjugated to psoralen. Biochemistry 2006;45:314-23.
Kocalka et al., Rapid and efficient DNA strand cross-linking by click chemistry. Chembiochem 2008;9:1280-5.
Kolb et al., The growing impact of click chemistry on drug discovery. Drug Discovery Today 2003;8(24):1128-37.
Krasia et al., Formation of oligotriazoles catalysed by cucurbituril. Chem. Commun. 2002:22-23.
Lanzavecchia et al., The use of hybrid hybridomas to target human cytotoxic T lymphocytes. Eur. J. Immunol. 1987;17:105-11.
Lewis et al., Discovery and characterization of catalysts for azide-alkyne cycloaddition by fluorescence quenching. J. Am. Chem. Soc. 2004;126:9152-3.
Li et al., Detection of single micron-sized magnetic bead and magnetic nanoparticles using spin valve sensors for biological applications. J. Appl. Phys. 2003;93(10):7557-9.
Li et al., Model and experiment of detecting multiple magnetic nanoparticles as biomolecular labels by spin valve sensors. IEEE Trans. Magn., 2004;40:3000-2.
Li et al., Selection of optimal oligonucleotide probes for microarrays using multiple criteria, global alignment and parameter estimation. Nucleic Acids Research 2005;33(19):6114-23.
Lin et al., Mechanistic investigation of the Staudinger ligation. J. Am. Chem. Soc. 2005;127:2686-95.
Long et al., Localized "click" chemistry through dip-pen nanolithography. Adv. Mat. 2007;19:4471-3.
Luo et al., Controlled assembly of dendrimer-like DNA. Nature Materials 2004;3:38-42.

(56) References Cited

OTHER PUBLICATIONS

Lynn et al., Water-soluble ruthenium alkylidenes: Synthesis, characterization, and application to olefin metathesis in protic solvents. J. Am. Chem. Soc. 2000;122: 6601-9.

Miller et al., A DNA array sensor utilizing magnetic microbeads and magnetoelectronic detection. J. Magn. Magn. Mater., 2001;225:138-44.

Mottes et al., Restoration by T4 ligase of DNA sequences sensitive to "flush"-cleaving restriction enzyme. Nucleic Acids Research 1977;4(7):2467-76.

Nagasaki et al., Photoenhancement of transfection efficiency using novel cationic lipids having a photocleavable spacer. Bioconjugate Chem. 2003;14:513-6.

Okamoto et al., Synthesis and properties of peptide nucleic acids containing a psoralen unit. Org. Lett. 2001;3(6):925-7.

Pendergrast et al., Determination of the orientation of a DNA binding motif in a protein-DNA complex by photocrosslinking. Proc. Nati. Acad. Sci. USA 1992;89:10287-91.

Praseuth et al., Double helices with parallel strands are formed by nuclease-resistant oligo-[α]-deoxynucleotides and oligo-[α]-deoxynucleotides covalently linked to an intercalating agent with complementary oligo-[β]-deoxynucleotides. J. Mol. Biol. 1987;196:939-42.

Praseuth et al., Sequence-specific binding and photocrosslinking of α and β oligodeoxynucleotides to the major groove of DNA via triple-helix formation. Proc. Natl. Acad. Sci. USA 1988;85:1349-53.

Rodionov et al., Mechanism of the ligand-free Cu(I)-catalyzed azide-alkyne cycloaddition reaction. Angrew. Chem. Int. Ed. 2005;44:2210-5.

Rostovtsev et al., A stepqise Huisgen cycloaddition process: Copper(I)-catalyzed regioselective "ligation" of azides and terminal alkynes. Angew. Chem. Int. Ed. 2002;41(14):2596-9.

Ruparel et al., Design and synthesis of a 3'-O-allyl photocleavable fluorescent nucleotide as a reversible terminator for DNA sequencing by synthesis. Proc. Natl. Acad. Sci. 2006;102(17):5932-7.

Saffran et al., Preparation and characterization of biotinylated psoralen. Nucleic Acids Research 1988;16(15):7221-31.

Salic et al., A chemical method for fast and sensitive detection of DNA synthesis in vivo. Proc. Natl. Acad. Sci. 2008;105(7):2415-20.

Saravis et al., Amplified immunoperoxidase staining of isoelectrically focused human tumor markers. Elecrophoresis 1980;1:191-3.

Saxon et al., Cell surface engineering by a modified Staudinger reaction. Science 2000;287(5460):2007-10.

Seol et al., Gold nanoparticles: enhanced optical trapping and sensitivity coupled with significant heating. Optics Letters 2006;31(16):2429-31.

Shchepinov et al., Oligonucleotide dendrimers: synthesis and sue as polylabelled DNA probes. Nucleic Acids Research 1997;25(22):4447-54.

Shchepinov et al., Oligonucleotide dendrimers: stable nano-structures. Nucleic Acids Research 1999;27(15):3035-41.

Shen et al., In situ detection of single micron-sized magnetic beads using magnetic tunnel junction sensors. Appl. Phys. Lett., 2005;86:253901(1-3).

Speel et al., Amplification methods to increase the sensitivity of in situ hybridization: Play CARD(S). J. Hist. Cyt. 1999;47(3):281-8.

Spielmann et al., DNA structural reorganization upon conversion of a psoralen furan-side monoadduct to an interstrand cross-link: Implications for DNA repair. Proc. Natl. Acad. Sci. USA 1995;92:2345-9.

Sugino et al, Interaction of bacteriophage T4 RNA and DNA ligases in joining of duplex DNA at base-paired ends. J. Biol. Chem. 1977;252(11):3987-94.

Tornoe et al., Peptidotriazoles on solid phase: [1,2,3]-Triazoles by regiospecific copper(I)-catalyzed 1,3-dipolar cycloadditions of terminal alkynes to azides. J. Org. Chem. 2002;67:3057-64.

Van De Sande et al., T4 polynucleotide ligase catalyzed joining of short synthetic DNA duplexes at base-paired ends. Biochemistry 1978;17(4):723-9.

Wang et al., Towards a magnetic microarray for sensitive diagnostics. J. Magn. Magn. Mater. 2005;293:731-6.

Wang et al., Bioconjugation by copper(I)-catalyzed azide-alkyne [3 + 2] cycloaddition. J. Am. Chem. Soc. 2003;125:3192-3.

Wittung et al., Interactions of DNA binding ligands with PNA-DNA hybrids. Nucleic Acids Research 1994;22 (24):5371-7.

Wu et al., Efficiency and fidelity in a click-chemistry route to triazole dendrimers by the copper(I)-catalyzed ligation of azides and alkynes. Angrew. Chem. Int. Ed. 2004;43:3928-32.

Yoo et al., Copper-catalyzed synthesis of N-sulfonyl-1,2,3-triazoles: Controlling selectivity. Angew. Chem. Int. Ed. 2007;46:1730-3.

IBM Almaden Research Center, Magnetic Tunnel Junctions (MTJs) (2006).

Schrag et al., Magnetic tunnel junction sensor development for industrial applications. Micro Magnetics, Inc. (2006).

Collins, et al., A branched DNA signal amplification assay for quantification of nucleic acid targets below 100 molecules/ml., Nucleic Acids Res. Aug. 1, 1997; 25(15): 2979-2984.

Wilson et al. "A multiplexed PCR-coupled liquid bead array for the simultaneous detection of four biothreat agents" Molecular and Cellular Probes 19(2):137 (2005).

Joshi et al. (2004) "A Three-Component Mannich Type Reaction for Selective Tyrosine Bioconjugation" J Am Chem Soc 126(49):15942-15943.

Martins et al. (2009) "Femtomolar Limit of Detection with a Magnetoresistive Biochip" Biosens Bioelectron 24(8):2690-2695.

U.S. Appl. No. 13/396,352, filed Feb. 14, 2012, Hu et al.

Webb, Thomas R., et al.; "Sequence-Specific Cross-Linking of Deoxyoligonucteoti via Hybridization-Triggered Alkylation"; J. Am. Chem. Soc. 108; (1986); pp. 2764-2765.

Graham et al. (2004) "Magnetoresistive-Based Biosensors and Biochips" Trends Biotechnol 22(9):455-462.

Gryaznov & Letsinger (1993) "Chemical Ligation of Oligonucleotides in the Presence and Absence of a Template" 115(9):3808-3809.

Lai et al. (1999) "Rapid, Femtomolar Bioassays in Complex Matrices Combining Microfluidics and Magnetoelectronics" Biosens Bioelectron 23(2):191-200.

Molecular Probes: Invitrogen Detection Technologies "Invitrogen Tyramide Signal Amplification Kit" Dec. 5, 2005, pp. 1-6.

Mulvaney et al. (2007) "Nucleic Acid-Based Cross-Linking Assay for Detection and Quantification of Hepatitis B Virus DNA" J Clin Microbiol 37(1):161-164.

\* cited by examiner

X (1st member of reactive pair)
Y (2nd member of reactive pair)

$X_1$ (1st member of a covalent bond forming reactive pair)
$X_2$ (2nd member of the covalent bond forming reactive pair)
······(covalent bond)

X (1st member of reactive pair)
Y (2nd member of reactive pair)
A & B (target-specific binding moieties)
⌠ (Optional covalent cross linker)

Direct Synthesis of a Branched Linking Molecule Comprising Multiple First Members of a Reactive Pair

Utilizing ODN synthesis and peptide synthesis chemistries to build the branched linking molecule directly on ODN P = activatable group for coupling reaction
X = removable protecting group
W = Member of Reactive Pair

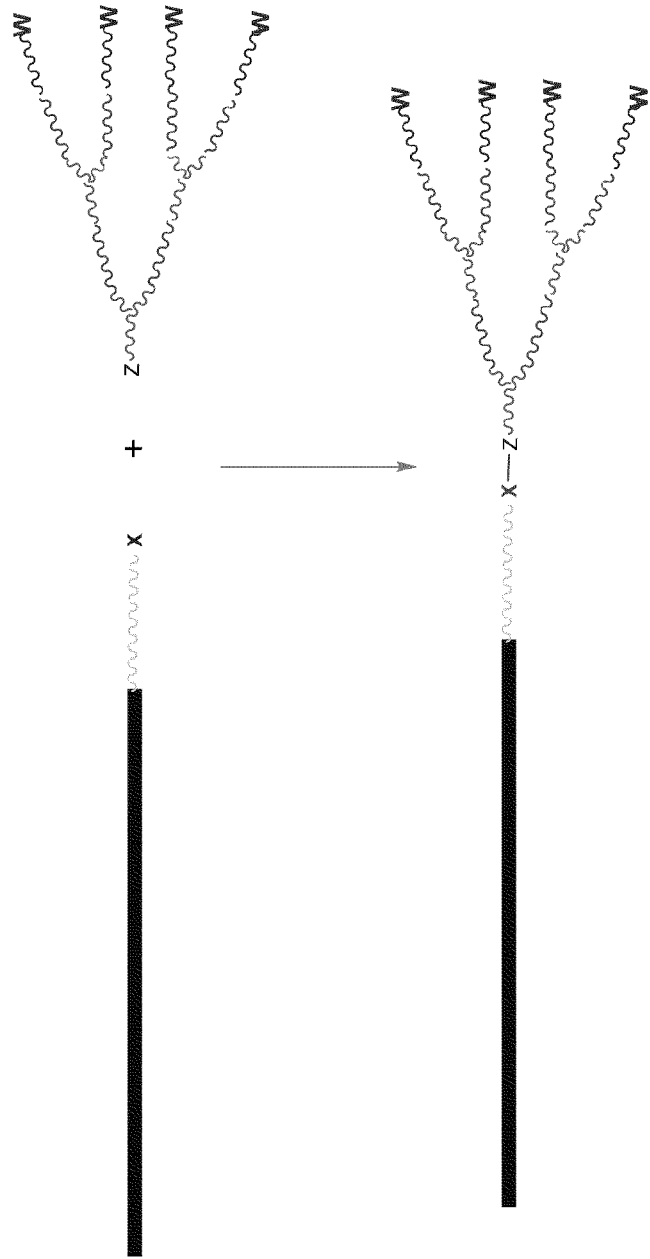

Figure 10

Conjugation of Branched Moiety with ODN to Form Linking Molecule

X and Z = functional groups suitable for conjugation using one of the following conjugation chemistries: Click chemistry, Thio and maleimide, thio and bromo-alkyl, aldehyde and hydrozine or hydrozide, amine and NHS ester, disulfide bond fomation, Diels-Alder Reaction, etc.

W = Member of Reactive Pair

Attachment of Multiple First Members of a Reactive Pair and Introduction of Coupling Linker on Dendrimer or Star Oligomer

METHODS AND COMPOSITIONS IN PARTICLE-BASED DETECTION OF TARGET MOLECULES USING COVALENT BOND FORMING REACTIVE PAIRS

CROSS REFERENCE TO RELATED APPLICATION

This application claims priority to U.S. Provisional Patent Application No. 61/115,401 filed Nov. 17, 2008, which is incorporated by reference in its entirety and for all purposes.

BACKGROUND

Magnetic sensing capabilities developed in electronics and semiconductor industries in applications such as the read heads in hard drives have seen great advancements in the last couple decades with higher sensitivity and density. In recent years there has been much interest in applying these capabilities to the detection of biomolecules. The present disclosure addresses these issues, and provides related advantages.

SUMMARY OF THE INVENTION

Methods and compositions which can be used to increase the strength and/or probability of forming a binding complex comprising a target molecule and a substrate are disclosed. In one aspect, linking molecules having one or more first members of a reactive pair are disclosed which can be used to increase the number of intra-complex binding interactions in a complex comprising a target molecule and a substrate. Intra-complex crosslinking and inter-complex crosslinking can be utilized in connection with these methods and compositions to further strengthen and stabilize the disclosed binding complexes.

In a first aspect, the present disclosure provides a method of generating a covalent binding complex comprising a target molecule, a linking molecule and a substrate, wherein the method comprises combining in a reaction mixture a substrate, a sample suspected of containing a target molecule, and a linking molecule. The substrate comprises a plurality of first members of a reactive pair and the linking molecule comprises one or more target-specific binding moieties which specifically bind to the target molecule, when present. When the linking molecule comprises multiple target-specific binding moieties, each of the target-specific binding moieties specifically binds to a different region of the target molecule when present. The linking molecule also comprises one or more second members of the reactive pair. The combining is under reaction conditions sufficient to provide for specific binding of the linking molecule to the target molecule, if present. The method further comprises subjecting the reaction mixture to conditions suitable for formation of covalent bonds between first members of the reactive pair and second members of the reactive pair, wherein, when the target molecule is present in the sample, the linking molecule specifically binds to the target molecule and forms one or more covalent bonds via reaction of one or more of the plurality of first members with the one or more second members of the reactive pair, thereby forming a complex comprising the target molecule, the linking molecule and the substrate.

In one embodiment, when the linking molecule comprises a single target-specific binding moiety, the linking molecule comprises a plurality of second members of the reactive pair, and when the linking molecule comprises a single second member of the reactive pair, the linking molecule comprises a plurality of the target-specific binding moieties.

The method can further comprise detecting the presence or absence of the complex.

In one embodiment, the method results in formation of the complex.

In one embodiment, the linking molecule comprises a plurality of the target-specific binding moieties and one of the second members of the reactive pair.

In another embodiment, the linking molecule comprises one of the target-specific binding moieties and a plurality of the second members of the reactive pair.

In another embodiment, the linking molecule comprises a plurality of the target-specific binding moieties and a plurality of the second members of the reactive pair.

In one embodiment, the substrate comprises a biochip surface.

In another embodiment, the substrate is a detectable label.

In one embodiment where the substrate is a detectable label, the detectable label is a magnetic particle.

In a second aspect of the present disclosure, an embodiment of the method described in the first aspect is disclosed, wherein the substrate is a detectable label, and wherein the method further comprises including in the reaction mixture a substrate comprising a biochip surface, wherein the biochip surface comprises a plurality of target-immobilization probes, and wherein the combining is under reaction conditions sufficient to provide for specific binding of the target molecule, if present, to one of the plurality of target-immobilization probes. When the target molecule is present in the sample, one of the plurality of target-immobilization probes specifically binds to the target molecule, the target molecule specifically binds to the linking molecule and the linking molecule forms one or more covalent bonds via reaction of one or more of the plurality of first members with the one or more second members of the reactive pair, thereby forming a complex comprising the biochip surface, one of the plurality of target-immobilization probes, the target molecule, the linking molecule and the detectable label.

In one embodiment of the method described in the second aspect of the present disclosure, each of the plurality of target-immobilization probes comprises one or more first members of the reactive pair, and the linking molecule forms one or more covalent bonds with one or more of the plurality of target-immobilization probes via reaction of one or more first members of the reactive pair with one or more second members of the reactive pair.

In another embodiment of the method described in the second aspect of the present disclosure, the method further comprises detecting the presence or absence of the complex comprising the biochip surface, one of the plurality of target-immobilization probes, the target molecule, the linking molecule and the detectable label.

In another embodiment of the method described in the second aspect of the present disclosure, the method results in formation of the complex comprising the biochip surface, one of the plurality of target-immobilization probes, the nucleic acid target molecule, the linking molecule and the detectable label.

In another embodiment of the method described in the second aspect of the present disclosure, the linking molecule comprises a plurality of the target-specific binding moieties and one of the second members of the reactive pair.

In another embodiment of the method described in the second aspect of the present disclosure, the linking molecule comprises one of the target-specific binding moieties and a plurality of the second members of the reactive pair.

In another embodiment of the method described in the second aspect of the present disclosure, the linking molecule comprises a plurality of the target-specific binding moieties and a plurality of the second members of the reactive pair.

In another embodiment of the method described in the second aspect of the present disclosure, a plurality of complexes are formed, wherein each member of the plurality comprises a biochip surface, one of the plurality of target-immobilization probes, a target molecule and a detectable label, and the method further comprises adding to the reaction mixture a cross-linking agent to link at least two of the plurality of complexes via one or more covalent bonds.

In another embodiment of the method described in the second aspect of the present disclosure, the detectable label is a magnetic particle.

In another embodiment of the method described in the second aspect of the present disclosure, the method further comprises cross-linking at least two members of the complex comprising the biochip surface, one of the plurality of target-immobilization probes, the target molecule, the linking molecule and the detectable label.

In a third aspect of the present disclosure, a method of generating a covalent binding complex comprising a target molecule, a linking molecule and a substrate is provided. The method comprises combining in a reaction mixture a substrate, a sample suspected of containing a target molecule, and a plurality of linking molecules. The substrate comprises a plurality of first members of a reactive pair. Each member of the plurality of linking molecules is independently present in one or more copies, and each member comprises a target-specific binding moiety which specifically binds to a different region of the target molecule, when present. Each member of the plurality of linking molecules also comprises a second member of the reactive pair. The combining is under reaction conditions sufficient to provide for specific binding of the plurality of linking molecules to the target molecule, if present. The method further comprises subjecting the reaction mixture to conditions suitable for formation of covalent bonds between first members of the reactive pair and second members of the reactive pair. When the target molecule is present in the sample, the plurality of linking molecules specifically binds to a plurality of different regions of the target molecule and forms a plurality of covalent bonds via reaction of the first members of the reactive pair with the second members of the reactive pair, thereby forming a complex comprising the target molecule, the plurality of linking molecules and the substrate.

In one embodiment of the method described in the third aspect of the present disclosure, the method further comprises detecting the presence or absence of the complex.

In another embodiment of the method described in the third aspect of the present disclosure, the method results in formation of the complex.

In another embodiment of the method described in the third aspect of the present disclosure, a plurality of complexes are formed, each member of the plurality comprising a biochip surface, a plurality of linking molecules, a target molecule, and a detectable label. The method further comprises adding to the reaction mixture a cross-linking agent to link at least two of the plurality of complexes via one or more covalent bonds.

In another embodiment of the method described in the third aspect of the present disclosure, the substrate comprises a biochip surface.

In another embodiment of the method described in the third aspect of the present disclosure, the substrate is a detectable label. In one such embodiment, the detectable label is a magnetic particle.

In a fourth aspect, the present disclosure provides a method as described in the third aspect of the present disclosure, wherein the substrate is a detectable label, and wherein the method further comprises including in the reaction mixture a substrate comprising a biochip surface. The biochip surface comprises a plurality of target-immobilization probes and the combining is under reaction conditions sufficient to provide for specific binding of the target molecule, if present, to one of the plurality of target-immobilization probes. When the target molecule is present in the sample, one of the plurality of target-immobilization probes specifically binds to the target molecule, the target molecule specifically binds to the plurality of linking molecules and the plurality of linking molecules forms a plurality of covalent bonds via reaction of the first members of the reactive pair with the second members of the reactive pair, thereby forming a complex comprising the biochip surface, one of the plurality of target-immobilization probes, the target molecule, the plurality of linking molecules and the detectable label.

In one embodiment of the method described in the fourth aspect of the present disclosure, each of the plurality of target-immobilization probes comprises one or more first members of the reactive pair, and one or more of the plurality of linking molecules forms one or more covalent bonds with one or more of the plurality of target-immobilization probes via reaction of one or more first members of the reactive pair with one or more second members of the reactive pair.

In another embodiment of the method described in the fourth aspect of the present disclosure, the method further comprises detecting the presence or absence of the complex comprising the biochip surface, one of the plurality of target-immobilization probes, the target molecule, the plurality of linking molecules and the detectable label.

In another embodiment of the method described in the fourth aspect of the present disclosure, the method results in formation of the complex comprising the biochip surface, one of the plurality of target-immobilization probes, the nucleic acid target molecule, the plurality of linking molecules and the detectable label.

In another embodiment of the method described in the fourth aspect of the present disclosure, a plurality of complexes are formed, wherein each member of the plurality comprises a biochip surface, one of the plurality of target-immobilization probes, a target molecule, a plurality of linking molecules and a detectable label, and wherein the method further comprises adding to the reaction mixture a cross-linking agent to link at least two of the plurality of complexes via one or more covalent bonds.

In another embodiment of the method described in the fourth aspect of the present disclosure, the detectable label is a magnetic particle.

In another embodiment of the method described in the fourth aspect of the present disclosure, the method further comprises cross-linking at least two members of the complex comprising the biochip surface, one of the plurality of target-immobilization probes, the target molecule, the plurality of linking molecules and the detectable label.

In a fifth aspect, the present disclosure provides a reaction mixture, wherein the reaction mixture comprises a substrate, a sample suspected of containing a target molecule, and a linking molecule. The substrate comprises a plurality of first members of a reactive pair. The linking molecule comprises one or more target-specific binding moieties which specifically bind to the target molecule, when present. When the linking molecule comprises multiple target-specific binding moieties, each of the target-specific binding moieties specifically binds to a different region of the target molecule when present. The linking molecule also comprises one or more second members of the reactive pair. When the target molecule is present in the sample, the linking molecule specifically binds to the target molecule and forms one or more covalent bonds via reaction of one or more of the plurality of first members with the one or more second members of the reactive pair, thereby forming a complex comprising the target molecule, the linking molecule and the substrate.

In one embodiment of the reaction mixture described in the fifth aspect of the present disclosure, when the linking molecule comprises a single target-specific binding moiety, the linking molecule comprises a plurality of second members of the reactive pair, and when the linking molecule comprises a single second member of the reactive pair, the linking molecule comprises a plurality of the target-specific binding moieties.

In another embodiment of the reaction mixture described in the fifth aspect of the present disclosure, the substrate comprises a biochip surface.

In another embodiment of the reaction mixture described in the fifth aspect of the present disclosure, the substrate is a detectable label. In one such embodiment, the detectable label is a magnetic particle.

In another embodiment of the reaction mixture described in the fifth aspect of the present disclosure, the linking molecule comprises a plurality of the target-specific binding moieties and one of the second members of the reactive pair.

In another embodiment of the reaction mixture described in the fifth aspect of the present disclosure, the linking molecule comprises one of the target-specific binding moieties and a plurality of the second members of the reactive pair.

In another embodiment of the reaction mixture described in the fifth aspect of the present disclosure, the linking molecule comprises a plurality of the target-specific binding moieties and a plurality of the second members of the reactive pair.

In a sixth aspect, the present disclosure provides a reaction mixture as described in the fifth aspect of the present disclosure, wherein the substrate is a detectable label, and wherein the reaction mixture further comprises a substrate comprising a biochip surface, wherein the biochip surface comprises a plurality of target-immobilization probes. When the target molecule is present in the sample, one of the target-immobilization probes specifically binds to the target molecule, the target molecule specifically binds to the linking molecule and the linking molecule forms one or more covalent bonds via reaction of one or more of the plurality of first members with the one or more second members of the reactive pair, thereby forming a complex comprising the biochip surface, one of the plurality of target-immobilization probes, the target molecule, the linking molecule and the detectable label.

In one embodiment of the reaction mixture described in the sixth aspect of the present disclosure, each of the plurality of target-immobilization probes comprises one or more first members of the reactive pair, and the linking molecule forms one or more covalent bonds with one or more of the plurality of target-immobilization probes via reaction of one or more first members of the reactive pair with one or more second members of the reactive pair.

In another embodiment of the reaction mixture described in the sixth aspect of the present disclosure, the detectable label is a magnetic particle.

In another embodiment of the reaction mixture described in the sixth aspect of the present disclosure, the linking molecule comprises a plurality of the target-specific binding moieties and one of the second members of the reactive pair.

In another embodiment of the reaction mixture described in the sixth aspect of the present disclosure, the linking molecule comprises one of the target-specific binding moieties and a plurality of the second members of the reactive pair.

In another embodiment of the reaction mixture described in the sixth aspect of the present disclosure, the linking molecule comprises a plurality of the target-specific binding moieties and a plurality of the second members of the reactive pair.

In a seventh aspect, the present disclosure provides a reaction mixture, wherein the reaction mixture comprises a substrate, a sample suspected of containing a target molecule, and a plurality of linking molecules. The substrate comprises a plurality of first members of a reactive pair. Each member of the plurality of linking molecules is independently present in one or more copies, and each member comprises a target-specific binding moiety which specifically binds to a different region of the nucleic acid target molecule, when present. Each member of the plurality of linking molecules also comprises a second member of the reactive pair. When the target molecule is present in the sample, the plurality of linking molecules specifically binds to a plurality of different regions of the target molecule and forms a plurality of covalent bonds via reaction of first members of the reactive pair with second members of the reactive pair, thereby forming a complex comprising the target molecule, the plurality of linking molecules, and the substrate.

In one embodiment of the reaction mixture described in the seventh aspect of the present disclosure, the substrate comprises a biochip surface.

In another embodiment of the reaction mixture described in the seventh aspect of the present disclosure the substrate is a detectable label. In one such embodiment, the detectable label is a magnetic particle.

In an eighth aspect, the present disclosure provides a reaction mixture as described in the seventh aspect of the present disclosure, wherein the substrate is a detectable label, and wherein the reaction mixture further comprises a substrate comprising a biochip surface. The biochip surface comprises a plurality of target-immobilization probes. When the target molecule is present in the sample, one of the plurality of target-immobilization probes specifically binds to the target molecule, the target molecule specifically binds to the plurality of linking molecules and the plurality of linking molecules forms a plurality of covalent bonds via reaction of the first members of the reactive pair with the second members of the reactive pair, thereby forming a complex comprising the biochip surface, one of the plurality of target-immobilization probes, the target molecule, the plurality of linking molecules and the detectable label.

In one embodiment of the reaction mixture described in the eighth aspect of the present disclosure, each of the plurality of target-immobilization probes comprises one or more first members of the reactive pair, and one or more of the plurality of linking molecules forms one or more covalent bonds with one or more of the plurality of target-immobilization probes via reaction of one or more first members of the reactive pair with one or more second members of the reactive pair.

In another embodiment of the reaction mixture described in the eighth aspect of the present disclosure, the detectable label is a magnetic particle.

In a ninth aspect, the present disclosure provides a kit, wherein the kit comprises a magnetic particle, and wherein the magnetic particle comprises a plurality of first members of a reactive pair. The kit further comprises a linking molecule, wherein the linking molecule comprises one or more target-specific binding moieties which specifically bind to a target molecule, when present. When the linking molecule comprises multiple target-specific binding moieties, each of the target-specific binding moieties specifically binds to a different region of the target molecule when present. The linking molecule also comprises one or more second members of the reactive pair.

In one embodiment of the kit described in the ninth aspect of the present disclosure, when the linking molecule comprises a single target-specific binding moiety, the linking molecule comprises a plurality of second members of the reactive pair, and wherein when the linking molecule comprises a single second member of the reactive pair, the linking molecule comprises a plurality of the target specific binding moieties.

In another embodiment of the kit described in the ninth aspect of the present disclosure, the kit further comprises a substrate comprising a biochip surface, wherein the biochip surface comprises a plurality of target-immobilization probes which specifically bind the target molecule when present.

In a tenth aspect, the present disclosure provides a method of forming a detectable covalent binding complex. The method comprises subjecting a sample suspected of containing a target molecule to conditions sufficient to produce a reaction mixture comprising a modified target molecule comprising a plurality of first members of a reactive pair. The method further comprises contacting the reaction mixture with a target-immobilization probe, wherein the contacting is under conditions suitable for formation of a non-covalent binding complex comprising the modified target molecule, if present, and the target-immobilization probe, and wherein the target-immobilization probe comprises a second member of the reactive pair. The method further comprises contacting the reaction mixture with a magnetic particle, wherein the magnetic particle comprises a second member of the reactive pair. The method further comprises subjecting the reaction mixture to conditions suitable for formation of covalent bonds between first and second members of the reactive pair, wherein, when the target molecule is present in the sample, a detectable covalent binding complex comprising the modified target molecule is formed.

In one embodiment of the method described in the tenth aspect of the present disclosure, the target molecule is a nucleic acid target molecule and the non-covalent binding complex comprising the modified target molecule, if present, and the target-immobilization probe, is formed as a result of a specific hybridization reaction.

In another embodiment of the method described in the tenth aspect of the present disclosure, the magnetic particle comprises a label probe and the second member of the reactive pair comprised by the magnetic particle is a component of the label probe.

In an eleventh aspect, the present disclosure provides a method as described in the tenth aspect of the present disclosure, wherein the magnetic particle comprises a label probe and the second member of the reactive pair comprised by the magnetic particle is a component of the label probe, and wherein the label probe is capable of forming a non-covalent binding complex with the modified target molecule, and wherein prior to subjecting the reaction mixture to conditions suitable for formation of one or more covalent bonds, the reaction mixture is subjected to conditions suitable for formation of a non-covalent binding complex comprising the magnetic particle, the modified target molecule and the target immobilization probe, such that, when the modified target molecule is present in the reaction mixture a non-covalent binding complex comprising the magnetic particle, the modified target molecule and the target-immobilization probe is formed.

In one embodiment of the method described in the eleventh aspect of the present disclosure, the target molecule is a nucleic acid target molecule and the non-covalent binding complex comprising the magnetic particle, the modified target molecule and the target-immobilization probe is formed as a result of specific hybridization reactions.

In one embodiment of the method described in the tenth aspect of the present discicosure, the method further comprises detecting the presence, absence and/or amount of the detectable covalent binding complex.

In another embodiment of the method described in the tenth aspect of the present disclosure, the covalent bond forming reactive pair is an azide/alkyne reactive pair, and the conditions suitable for formation of the covalent bonds comprise contacting the reaction mixture with a Cu ion catalyst.

In another embodiment of the method described in the tenth aspect of the present disclosure, the method further comprises contacting the reaction mixture with a nucleic acid cross-linking reagent.

BRIEF DESCRIPTION OF THE DRAWINGS

The disclosure is best understood from the following detailed description when read in conjunction with the accompanying drawings. It is emphasized that, according to common practice, the various features of the drawings are not necessarily to-scale. The dimensions of the various features are arbitrarily expanded or reduced for clarity. Included in the drawings are the following figures.

FIG. 2A illustrates covalent bond formation between $1^{St}$ members of a reactive pair and $2^{nd}$ members of the reactive pair, wherein $2^{nd}$ members of the reactive pair are comprised by both the detectable label and the target immobilization probes, and the $1^{St}$ members are comprised by the linking molecules. Although FIG. 2A indicates a nucleic acid target molecule, such indication is for illustrative purposes only. Additional exemplary targets include, but are not limited to proteins and other biological entities.

FIG. 2B illustrates covalent bond formation between 1$^{st}$ members of a reactive pair ($X_1$) and 2$^{nd}$ members of the reactive pair ($X_2$), wherein 1st members of the reactive pair are comprised by both the detectable label and the target immobilization probes, and the 2nd members are comprised by the linking molecules.

In FIG. 6, a linking molecule is not required. Instead, a nucleic acid target is amplified via PCR with a modified base to introduce first members of the reactive pair. These 1$^{st}$ members react with second members of the reactive pair which are comprised by the target immobilization probe and a label probe present on the magnetic particle. Target nucleic acid is amplified via PCR with a modified base to introduce first members of a reactive pair, denoted X, into the resultant amplicon (inset). (i) The modified amplicon hybridizes specifically to a target-immobilization probe on the biochip surface. The target-immobilization probe (A) is modified with one or more second members of the reactive pair, denoted Y, that are capable of forming a covalent bonds with the first members of the reactive pair. (ii) The non-covalent structure (B) is incubated with magnetic particles functionalized with second members of the reactive pair (Y) under suitable conditions to covalently "fix" the structure "C." The presence of the magnetic particles is subsequently detected by the MTJ sensor array. "n" indicates a plurality of the bracketed members.

FIG. 10 illustrates a conjugation reaction between an ODN and a branched moiety to form a linking molecule comprising multiple first members of a reactive pair.

DEFINITIONS

Figure 1:
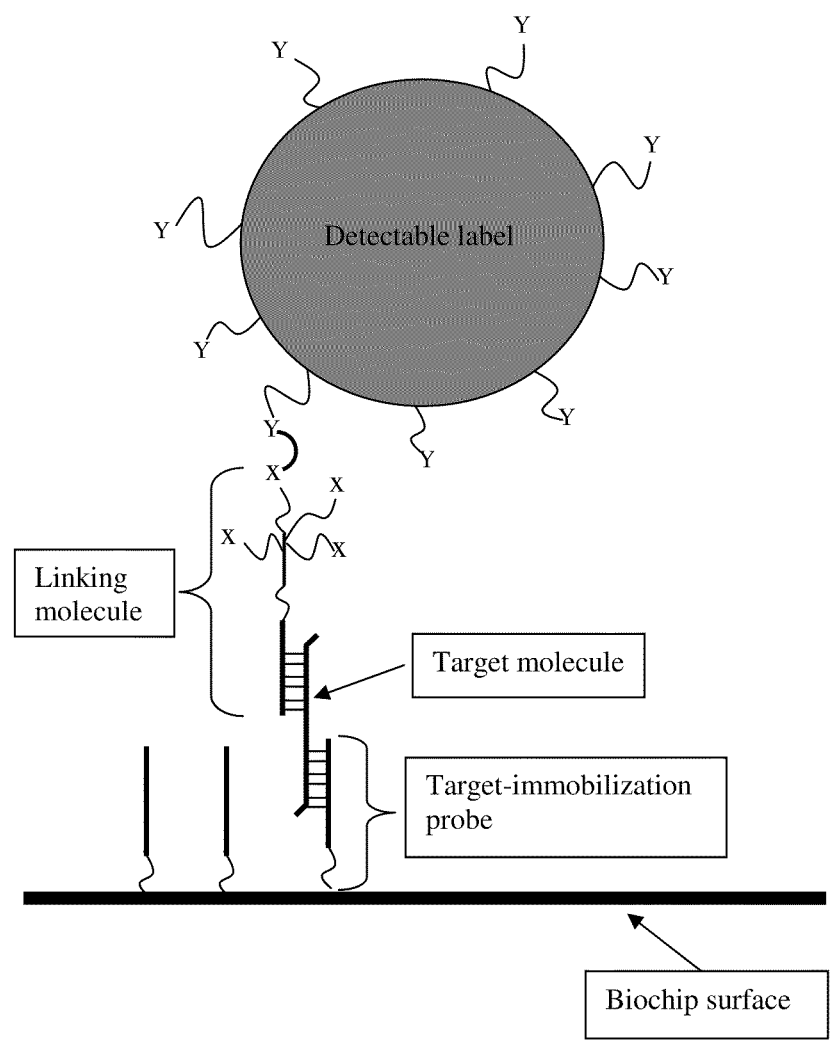
FIG. 1 provides an illustration of a binding complex comprising a target-immobilization probe, a nucleic acid target molecule, a linking molecule, a detectable label, and a substrate comprising a biochip surface.

Depending on the context, the term "substrate" as used herein refers to a substrate that can serve as a detectable label (or be modified to serve as a detectable label), e.g., a magnetic particle, or a substrate comprising a biochip surface which can be used to immobilize a target molecule for subsequent detection.

As used herein the term "biochip" refers to a solid, normally substantially planar support having a surface that is functionalized with an array of biological molecules capable of binding to other biological molecules of interest. A variety of materials can be used in the preparation of biochips including, e.g., glass slides, fused silica, silicon and plastic. In particular embodiments disclosed herein, biochips of interest comprise magnetic sensors capable of detecting the presence of a magnetic particle bound to a target molecule immobilized on the surface of the biochip. See, for example, Baselt et al., (1998) Biosens. Bioelectron., vol. 13, pp. 731-739; Edelstein et al., (2000) Biosens. Bioelectron., vol. 14, pp. 805-813; Miller et al., (2001) J. Magn. Magn. Mater., vol. 225, pp. 138-144; Graham et al. (2002) J. Appl. Phys., vol. 91, pp. 7786-7788; Ferreira et al. (2003) J. Appl. Phys., vol. 93, pp. 7281; Li et al. (2003) J. Appl. Phys., vol. 93, pp. 7557-7559, May; Li et al. (2004) IEEE Trans. Magn., vol. 40, pp. 3000; Wang et al., (2005) J. Magn. Magn. Mater., vol. 293, pp. 731-736; Shen et al. (2005) Appl. Phys. Lett., vol. 86, pp. 253901; Baselt et al. U.S. Pat. No. 5,981,297; Tondra, U.S. Pat. No. 6,743,639; and Tondra U.S. Pat. No. 6,875,621.

As used herein, the term "detectable label" refers to a molecule or particle capable of detection, including, but not limited to, radioactive isotopes, fluorescers, chemiluminescers, chromophores, enzymes, enzyme substrates, enzyme cofactors, enzyme inhibitors, dyes, metal ions, magnetic particles, members of a specific binding pair and the like.

The term "linking molecule" is used herein to refer to a molecule comprising at least one "member of a reactive pair" and at least one "target-specific binding moiety." The word "molecule" when used in the context of a linking molecule is not limited to a single molecular entity and can include a plurality of molecules bound to one another to produce the linking molecule.

The term "member of a reactive pair" is used herein to refer to first or second functional group, wherein the first and second functional groups react with one another under suitable conditions to form a covalent bond. Such reactive pairs may also be referred to as "covalent bond forming reactive pairs." It should be noted that when either member of the reactive pair is referred to as the first member, the remaining member is understood to be the second member and vice versa. Examples of first and second members of covalent bond forming reactive pairs include Cu-catalyzed azide/alkyne [3+2] cycloaddition "Click Chemistry" as described by Rostovtsev et al. (2002) *Angew. Chem. Int. Ed.* 41: 2596-2599 and Tornoe et al. (2002) *J. Org. Chem.* 67: 3057-3064; azide/DIFO (Difluorinated Cyclooctyne) Cu-free Click Chemistry as described by Baskin et al. (2007) *PNAS Vol.* 104, No. 43: 167393-16797; azide/phosphine "Staudinger Reaction" as described by Lin et al. (2005) *J. Am. Chem. Soc.* 127: 2686-2695; azide/triarylphosphine "Modified Staudinger Reaction" as described by Saxon and Bertozzi (2000) March 17 Science 287(5460):2007-10; and catalyzed olefin cross metathesis reactions as described by Casey (2006) *J. of Chem. Edu. Vol.* 83, No. 2: 192-195, Lynn et al. (2000) *J. Am. Chem. Soc.* 122: 6601-6609, and Chen et al. (2003) *Progress in Chemistry* 15: 401-408.

In some embodiments, "click chemistry functional groups" are of particular interest as first and second members of a reactive pair. The term "click chemistry function group" refers to an azide functional group or an alkyne functional group capable of participating in a covalent bond forming reaction with an alkyne function group or an azide functional group respectively. The term "click chemistry functional group" is also used herein to refer to an azide functional group or a DIFO functional group capable of participating in a covalent bond forming reaction with a DIFO functional group or an azide functional group respectively. It should be noted that while the azide/alkyne covalent bond forming reaction requires the presence of a Cu ion catalyst, the azide/DIFO covalent bond forming reaction does not require the use of such a catalyst.

The term "target-specific binding moiety" is used herein to refer a region of a linking molecule that is capable of specifically binding to a target molecule or other analyte of interest when brought into contact with the target molecule or other analyte of interest.

The term "target-immobilization probe" is used herein to refer to an entity bound to a surface of a substrate, e.g., a biochip, wherein the entity is capable of specifically binding to a target molecule when bought into contact with the target molecule.

The term "label probe" is used herein to refer to a molecule coupled to a detectable label, wherein the molecule is capable of binding specifically and at least non-covalently to a target molecule when brought into contact with the target molecule. In some embodiments described herein, label probes comprise one or more first or second members of a reactive pair.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "nucleic acid," "nucleic acid molecule" and "polynucleotide" are used interchangeably and refer to a polymeric form of nucleotides of any length, either deoxyribonucleotides or ribonucleotides, or compounds produced synthetically which can hybridize with naturally occurring nucleic acids in a sequence specific manner similar to that of two naturally occurring nucleic acids, e.g., can participate in Watson-Crick base pairing interactions. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, cDNA, recombinant polynucleotides, plasmids, vectors, isolated DNA of any sequence, control regions, isolated RNA of any sequence, nucleic acid probes, and primers.

The term "moiety" is used to refer to a portion of an entity or molecule, typically having a particular functional or structural feature.

The terms "antibody," "immunoglobulin" and their plural referents include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the terms are Fab', Fv, F(ab')2, and or other antibody fragments that retain specific binding to antigen.

Antibodies can be in a variety of forms including, for example, Fv, Fab, and (Fab')2, as well as bi-functional (i.e. bi-specific) hybrid antibodies (e.g., Lanzavecchia et al., *Eur. J. Immunol.* 17, 105 (1987)) and in single chains (e.g., Huston et al., Proc. Natl. Acad. Sci. U.S.A., 85, 5879-5883 (1988); Bird et al., Science, 242, 423-426 (1988); see Hood et al., "Immunology", Benjamin, N.Y., 2nd ed. (1984), and Hunkapiller and Hood, *Nature,* 323, 15-16 (1986)).

The terms "specific binding," "specifically bind," and the like, refer to the ability of a first binding molecule or moiety (e.g., a target-specific binding moiety or first member of a specific binding pair) to preferentially bind (covalently or non-covalently) to a second binding molecule or moiety (e.g., a target molecule or second member of a specific binding pair) relative to other molecules or moieties in a reaction mixture. For example, in certain embodiments involving protein-protein binding interactions, the affinity between a first binding molecule or moiety and a second binding molecule or moiety when they are specifically bound to each other in a binding complex is characterized by a KD (dissociation constant) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M.

As used herein, a "member of a specific binding pair" is a member of a specific binding pair interaction. It should be noted that when either member of the binding pair is referred to as the first member, the remaining member is understood to be the second member and vice versa. Examples of specific binding pair interactions include immune binding interactions such as antigen/antibody and hapten/antibody as well as non-immune binding interactions such as complementary nucleic acid binding, biotin/avidin and biotin/streptavidin.

The terms "capable of hybridizing," "hybridizing" and "hybridization" as used herein refer to a "specific binding" interaction between complementary or partially complementary nucleic acid molecules (e.g., DNA-DNA, RNA-DNA, RNA-RNA).

The term "complementary" references a property of specific binding between polynucleotides based on the sequences of the polynucleotides. As used herein, polynucleotides are complementary if they bind to each other in a hybridization assay under stringent conditions, e.g. if they produce a given or detectable level of signal in a hybridization assay. Portions of polynucleotides are complementary to each other if they follow conventional base-pairing rules, e.g. A pairs with T (or U) and G pairs with C. "Complementary" includes embodiments in which there is an absolute sequence complementarity, and also embodiments in which there is a substantial sequence complementarity.

"Absolute sequence complementarity" means that there is 100% sequence complementarity between a first polynucleotide and a second polynucleotide, i.e. there are no insertions, deletions, or substitutions in either of the first and second polynucleotides with respect to the other polynucleotide (over the complementary region). Put another way, every base of the complementary region is paired with its complementary base following normal base-pairing rules.

"Substantial sequence complementarity" permits one or more relatively small (less than 10 bases, e.g. less than 5 bases, typically less than 3 bases, more typically a single base) insertions, deletions, or substitutions in the first and or second polynucleotide (over the complementary region) relative to the other polynucleotide. The complementary region is the region that is complementary between a first polynucleotide and a second polynucleotide (e.g. a distinct sequence of a nucleic acid target molecule and a binding moiety of a linking molecule). Complementary sequences are typically embedded within larger polynucleotides, thus two relatively long polynucleotides may be complementary over only a portion of their total length. The complementary region is typically at least about 10 bases long, more typically at least about 12 bases long, more typically at least about 15 bases long, still more typically at least about 20 bases long, or may be at least about 25 bases long.

Hybridization as described herein in the context of nucleic acid hybridization typically occurs under "stringent conditions." The term "stringent conditions" refers to conditions under which a first nucleic acid will hybridize preferentially to a second nucleic acid sequence, and to a lesser extent to, or not at all to, other sequences. Put another way, the term "stringent hybridization conditions" as used herein refers to conditions that are compatible to produce duplexes between complementary binding members, e.g., between a binding moiety of a linking molecule and a complementary sequence of a target nucleic acid.

"Stringent hybridization conditions" and "stringent hybridization wash conditions" in the context of nucleic acid hybridization (e.g., as in array, Southern or Northern hybridizations) are sequence dependent, and are different under different environmental parameters. Stringent hybridization conditions can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO$_4$, 7% sodium dodecyl sulfate (SDS), 1 mnM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions may affect the degree to which nucleic acid molecules specifically hybridize. Suitable wash conditions may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 1 to about 20 minutes; or, multiple washes with a solution with a salt concentration of about 0.1×SSC containing 0.1% SDS at 20 to 50° C. for 1 to 15 minutes; or, equivalent conditions. Stringent conditions for washing can also be, e.g., 0.2×SSC/

0.1% SDS at 42° C. In instances wherein the nucleic acid molecules are oligodeoxynucleotides (e.g. oligonucleotides made up of deoxyribonucleotide subunits), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos). See Sambrook, et al., *Molecular Cloning: A Laboratory Manual*, Second Edition, (1989) Cold Spring Harbor, N.Y.), for detailed descriptions of equivalent hybridization and wash conditions and for reagents and buffers, e.g., SSC buffers and equivalent reagents and conditions.

Stringent hybridization conditions may also include a "prehybridization" of aqueous phase nucleic acids with complexity-reducing nucleic acids to suppress repetitive sequences. For example, certain stringent hybridization conditions include, prior to any hybridization to surface-bound polynucleotides, hybridization with Cot-1 DNA or with random sequence synthetic oligonucleotides (e.g. 25-mers), or the like.

Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

The terms "bind" and "bound" as used herein refers to a binding interaction between two or more entities. Where two entities, e.g., molecules, are bound to each other, they may be "directly bound," e.g., through covalent bonds, ionic bonds, hydrogen bonds, electrostatic interactions, hydrophobic interactions, Van der Waals forces, or a combination thereof, or they may be "indirectly bound," e.g., through the use of an intermediate linking moiety.

The terms "detect", "detecting" and the like encompass quantitative as well as qualitative measurements.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. It should be noted that the use of the term "preferred" in this context is not intended to limit the scope of the invention in any way. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a linking molecule" includes a plurality of such linking molecules and reference to "the binding complex" includes reference to one or more binding complexes and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The following detailed description is put forth so as to provide those of ordinary skill in the art with a complete disclosure and description of how to make and use the present invention, and is not intended to limit the scope of what the inventors regard as their invention. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s) and the like.

DETAILED DESCRIPTION

The present disclosure is directed to methods and compositions which can be used to increase the strength of and/or probability of forming a binding complex comprising a target molecule and a substrate. In one aspect, linking molecules are disclosed which can be used to increase the number of intra-complex binding interactions. Inter-complex cross-linking, i.e., cross-linking of two-or more different binding complexes, can be utilized in connection with these methods to further strengthen and stabilize the disclosed binding complexes.

Creating a Target Molecule-Substrate Complex Having Multiple Intra-Complex Binding Interaction Sites In one aspect, the present disclosure is directed to methods and compositions which may be utilized to create binding complexes comprising a target molecule and one or more substrates, wherein the binding complexes have multiple intra-complex binding interaction sites. One or more linking molecules are utilized to create the multiple intra-complex binding interaction sites in the target molecule-substrate binding complexes. In some embodiments, one or more linking molecules are used to provide multiple intra-complex binding interaction sites in a binding complex comprising a target molecule and a detectable label. In other embodiments, one or more linking molecules are used to provide multiple intra-complex binding interaction sites in a binding complex comprising a target molecule and a biochip surface. These embodiments can be employed either separately or together in a particular assay, e.g., an assay designed to detect the presence, absence and/or quantity of a target molecule.

Where one or more linking molecules are used to provide multiple intra-complex binding interaction sites in a binding complex comprising a target molecule and a detectable label, the linking molecules may be designed such that one or more detectable label entities bind the target molecule via the linking molecule or molecules. For example, in one embodiment only a single detectable label entity, e.g., a single magnetic particle, is bound to a particular target molecule via the linking molecule or molecules. In other embodiments, multiple detectable label entities are bound to a particular target molecule via the linking molecule or molecules.

A variety of molecular targets may be utilized in connection with the presently disclosed methods and compositions including, but not limited to, nucleic acid and protein targets.

Nucleic Acid Linking Molecules

Where the target molecule is a nucleic acid, nucleic acid linking molecules can be used to form a nucleic acid target molecule-substrate complex having multiple intra-complex binding sites. One type of nucleic acid linking molecule of interest comprises a single target-specific binding moiety which specifically hybridizes under suitable conditions to a nucleic acid target molecule of interest. Such nucleic acid linking molecules also comprise one or more first members of a reactive pair, wherein first members of the reactive pair react with second members of the reactive pair under suitable conditions to form covalent bonds. Other nucleic acid linking molecules of interest comprise multiple target-specific binding moieties, wherein each target specific binding moiety specifically hybridizes under suitable conditions to a different region of a nucleic acid target molecule of interest. Such nucleic acid linking molecules also comprise one or more first members of a reactive pair, wherein first members of the reactive pair react with second members of the reactive pair under suitable conditions to form covalent bonds.

A plurality of nucleic acid linking molecules can be used, wherein each nucleic acid linking molecule of the plurality of nucleic acid linking molecules comprises a target-specific binding moiety. Each target-specific binding moiety comprises a nucleic acid sequence capable of hybridizing specifically to a distinct sequence of the nucleic acid target molecule. Each of the plurality of linking molecules also comprises a first member of a reactive pair capable of reacting under suitable conditions with a second member of the reactive pair to form a covalent bond. Generally, the substrate comprises a plurality of such second members of the reactive pair. The plurality of linking molecules is designed such that it is capable of binding to a plurality of different regions of the target molecule and forming a plurality of covalent bonds with the second members of the reactive pair bound to the substrate. In this manner, a nucleic acid target molecule-substrate complex having multiple intra-complex binding sites can be formed.

Figure 2A:
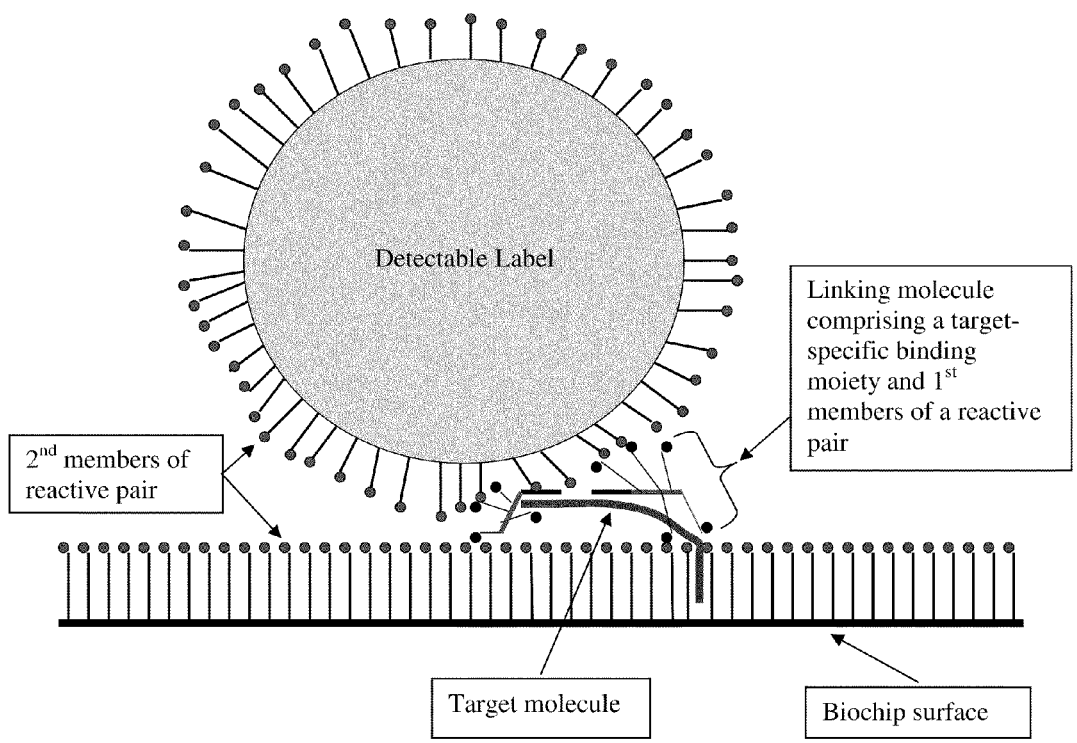
FIG. 2A provides an illustration of a binding complex comprising, a target-immobilization probe, a nucleic acid target molecule, a plurality of linking molecules, a detectable label and a substrate comprising a biochip surface.

FIGS. 1 and 2A illustrate binding interactions utilizing specific embodiments of the nucleic acid linking molecules disclosed herein.

FIG. 1 shows the utilization of two different substrates. The first substrate is a detectable label, e.g., a magnetic particle, and the second substrate comprises a biochip surface comprising a target-immobilization probe. In this example, the linking molecule comprises a single target-specific binding moiety comprising a nucleic acid sequence capable of hybridizing specifically with the nucleic acid target molecule of interest. The linking molecule comprises a plurality of first members of a reactive pair designated by "X" in the figure. These first members are capable of forming covalent bonds under suitable conditions with second members of the reactive pair designated by "Y" in the figure.

FIG. 2A also shows the utilization of a detectable label and a substrate comprising a biochip surface. FIG. 2A shows a binding complex comprising, a target-immobilization probe, a nucleic acid target molecule, a plurality of linking molecules, a detectable label and a substrate comprising a biochip surface. Each of the plurality of linking molecules shown in FIG. 2A comprises a single target specific binding moiety and a plurality of $1^{st}$ members of a specific binding pair. FIG. 2A illustrates covalent bond formation between the $1^{st}$ members of the reactive pair and $2^{nd}$ members of the reactive pair, wherein $2^{nd}$ members of the reactive pair are comprised by both the detectable label and the target immobilization probes. This configuration allows for increased binding strength though covalent bonds formed between the linking molecules and the detectable label and covalent bonds formed between the linking molecules and the target-immobilization probes on the substrate comprising the biochip surface.

Where a plurality of linking molecules is utilized, the plurality of linking molecules may be contacted to the target molecule (or a sample suspected of containing the target molecule) prior to contacting with the substrate so that the positioning of the linking molecules relative to the target molecule, prior to binding with the target molecule, is not significantly affected by the positions at which the linking molecules bind the substrate via members of a reactive pair.

Preparation of Nucleic Acid Linking Molecules

The target-specific binding moieties of the presently disclosed linking molecules can comprise DNA, RNA, their analogues, modified nucleotides or combinations thereof.

The binding moieties of the linking molecules can be covalently linked directly to each other through phosphodiester bonds or through one or more other agents such as nucleic acid, amino acid, carbohydrate or polyol bridges, or through other cross-linking agents that are capable of cross-linking nucleic acid or modified nucleic acid strands. The site(s) of linkage can be at the ends of the binding moieties and/or at one or more internal nucleotides in the strand.

The binding moieties of the presently disclosed linking molecules can comprise nucleic acid sequences of about 10 to about 80 nucleotides in length. For example, the first and/or second binding moieties can comprise nucleic acid sequences of about 10 to about 20, about 20 to about 30, about 30 to about 40, about 40 to about 50, about 50 to about 60, about 60 to about 70, or about 70 to about 80 nucleotides in length. More typically, the first and/or second binding moieties of the presently disclosed linking molecules comprise sequences of about 10 to about 60 nucleotides in length, even more typically about 10 to about 45 nucleotides in length.

Where a disclosed linking molecule comprises a plurality of target-specific binding moieties, this plurality can include, e.g., 2 or more, 3 or more, 4 or more, 5 or more, 6 or more, 7 or more, 8 or more, 9, or more, or 10 or more target-specific binding moieties.

Where a disclosed linking molecule comprises a plurality of first members of a reactive pair, this plurality can include e.g., 2 or more, 3 or more, 4 or more, 5 or more, 6 or more, 7 or more, 8 or more, 9 or more, or 10 or more first members of a reactive pair.

In some embodiments, the nucleic acid linking molecules disclosed herein are prepared in a linear configuration. Linear nucleic acid linking molecules can be prepared using a variety of techniques known in the art. For example, the linking molecules can be prepared by polymerase amplification, e.g., PCR, cloning techniques, chemical cross-linking, enzymatic assembly, direct chemical synthesis, or combinations thereof.

Where nucleic linking molecules are prepared by polymerase amplification or cloning, nucleic acid sequences that encode the entire linking molecule or fragments thereof can be made in single- or double-stranded form by conventional procedures. When made in double-stranded form, the linking molecules and/or fragments thereof are ultimately denatured or digested by exonuclease to provide single-stranded linking molecules and/or fragments thereof. Nucleic acid linking molecules can also be cloned in single-stranded form using conventional single-stranded phage vectors such as M13. Fragments can be linked enzymatically or chemically to form the linking molecule. When assembled enzymatically, the individual fragments can be ligated with a ligase such as T4 DNA or RNA ligase. When prepared by chemical cross-linking, the individual fragments can be synthesized with one or more nucleic acids that have been derivatized to have functional groups that provide linking sites or the fragments can be derivatized after the fragments have been synthesized to provide such sites.

The linking molecules of the present disclosure can also be designed and constructed in a branched configuration. Branched linking molecules are differentiated from linear linking molecules in that branched linking molecules have at least 3 termini, which can be 5' termini, 3' termini or a combination thereof. Methods of preparing branched nucleic acid molecules are provided in U.S. Pat. No. 5,124,246, issued Jun. 23, 1992, columns 8-13 and 18-25 of which are incorporated by reference herein for their description of branched multimer preparation. Additionally, U.S. Pat. No. 5,580,731, issued Dec. 3, 1996, is incorporated by reference herein for its description of N-4 modified pyrimidine nucleotides which can be used in the synthesis of the presently disclosed branched linking molecules.

Branched linking molecules can also be prepared in the form of dendrimeric oligonucleotides. See, for example, Shchepinov et al. (1997) *Nucleic Acids Research* 25(22): 4447-4454, wherein the authors describe the synthesis of a dendrimeric head on top of a conventional monomeric oligonucleotide utilizing a branched phosphoramidite with multiple protected primary hydroxyl groups. See also, Shchepinov et al. (1999) *Nucleic Acids Research* 27(15): 3035-3041, describing additional types of dendrimeric oligonucleotides and their preparation. These references are incorporated herein by reference for their description of dendrimeric oligonucleotides and preparation of same.

Additionally, branched linking molecules can be prepared using a combination of avidin/streptavidin and biotinylated nucleic acids. For example, an individual avidin/streptavidin molecule can be linked to four biotinylated nucleic acids via the avidin/streptavidin-biotin interaction. Linking molecules of this type can be prepared such that one of the four biotinylated nucleic acids comprises a nucleic acid sequence capable of specifically hyrbidizing to a distinct region of a nucleic acid target molecule of interest, while the remaining three biotinylated nucleic acids comprise nucleic acids functionalized with first members of a reactive pair.

Nucleic acid linking molecules can also be prepared using chemical or enzymatic techniques such as conjugation, ligation and polymerization. These chemical or enzymatic techniques can be applied to form multiple sites in both linear and various branched formations.

FIGS. 8-12 illustrate synthesis schemes for various "branched" and "star" linking molecules comprising an oligodeoxynucleotide (ODN) (or analogue thereof) target-specific binding moiety and multiple first members of a reactive pair. These linking molecules can be prepared via direct synthesis on an ODN (or analogue thereof) or through a two step synthesis process in which a branched or star moeity comprising biotin molecules is prepared separately from a modified ODN (or analogue thereof) and the two components are subsequently conjugated to form a linking molecule comprising a target-specific binding moiety and multiple first members of a reactive pair.

Figure 8:
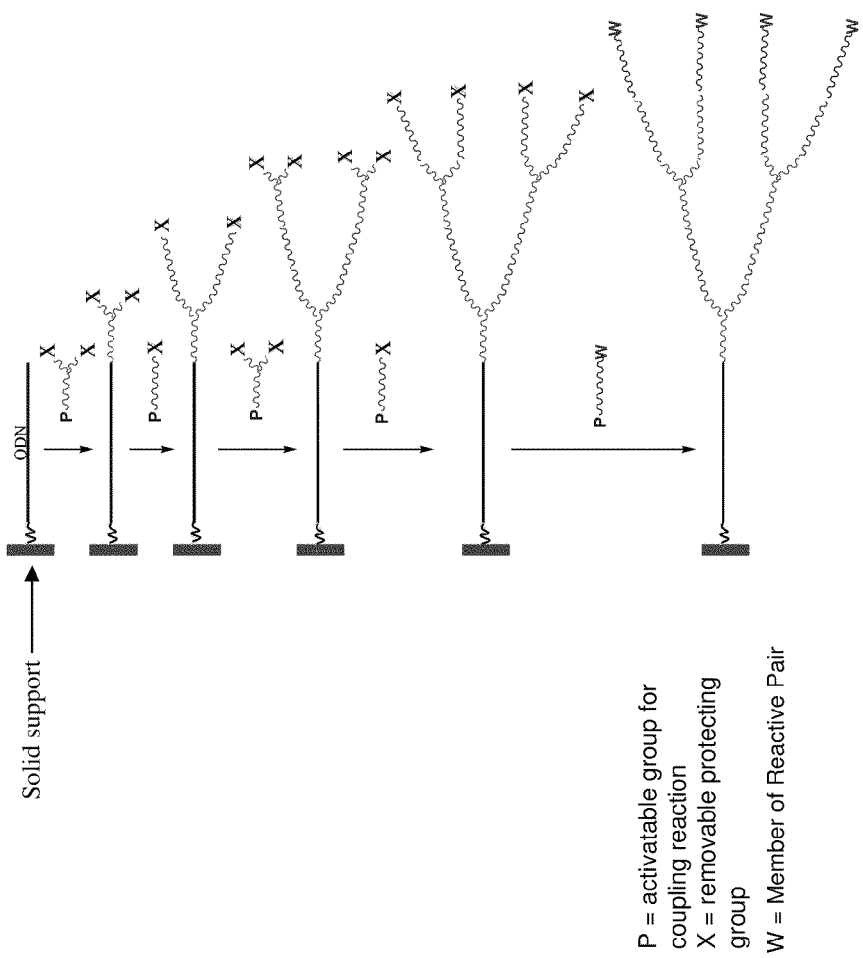
FIG. 8 illustrates a synthesis scheme for the direct synthesis of a branched linking molecule comprising multiple first members of reactive pair.

FIG. 8 shows a direct synthesis scheme for the preparation of a branched linking molecule in which a branched moiety is synthesized directly onto an ODN bound to a solid support. The branched linking molecule can be synthesized via a variety known solid support or in situ synthesis methods.

Figure 9:
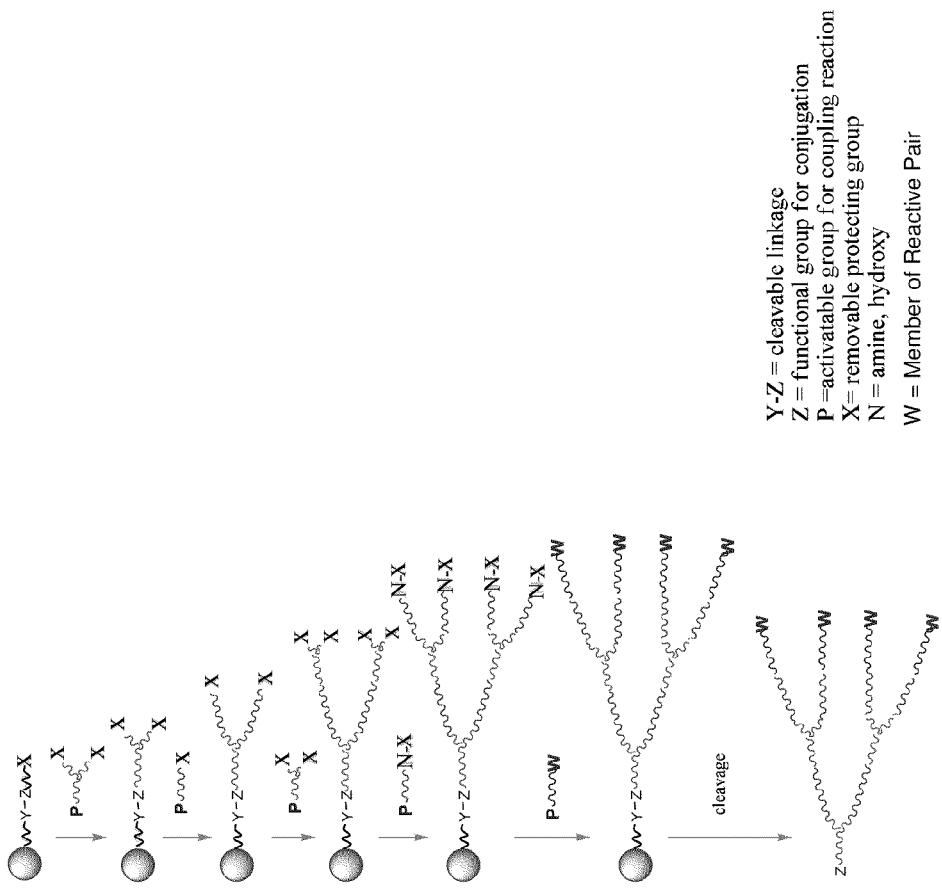
FIG. 9 illustrates a synthesis scheme for the synthesis of a branched moiety comprising multiple first members of a reactive pair.

FIG. 9 shows the synthesis of a branched moiety comprising multiple first members of a reactive pair. This branched moiety can then be conjugated to an ODN to form a linking molecule as illustrated in FIG. 10. A variety of functional groups and conjugation chemistries are available to facilitate this conjugation, e.g., Click chemistry, Thio and maleimide, thio and bromo-alkyl, aldehyde and hydrazine or hydrazide, amine and NHS ester, disulfide bond fomation, Diels-Alder Reaction, etc. The functional groups of these reactions are designated X and Z in FIG. 10.

Figure 11:
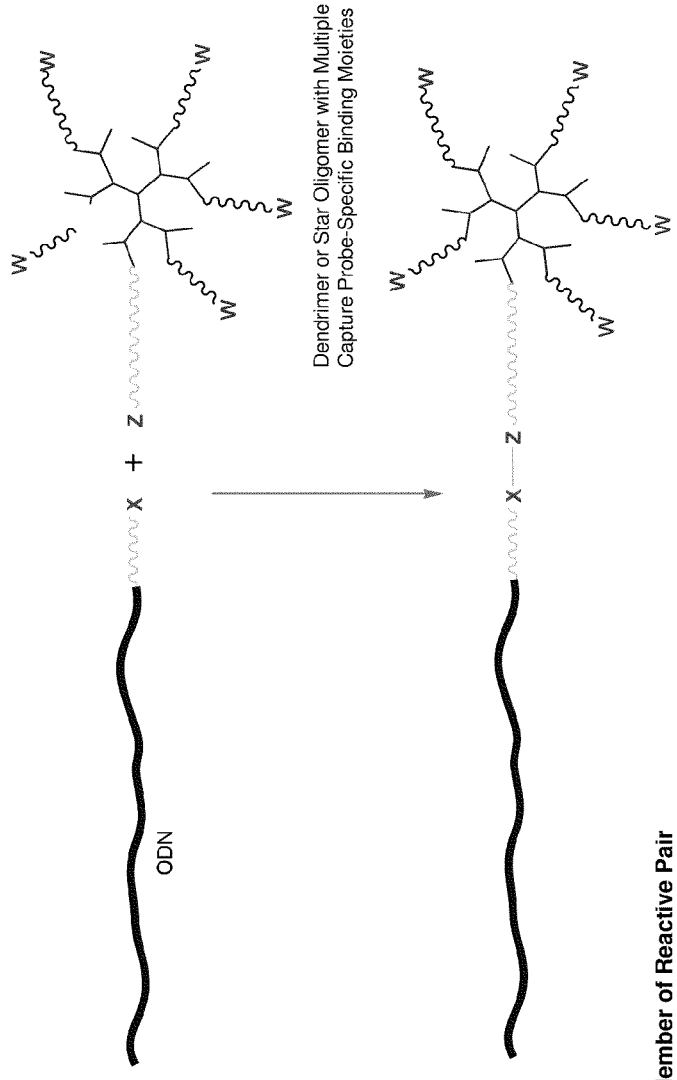
FIG. 11 illustrates the formation of a linking molecule by conjugation of ODN to dendrimer or star oligomer comprising multiple first members of a reactive pair.
Figure 12:
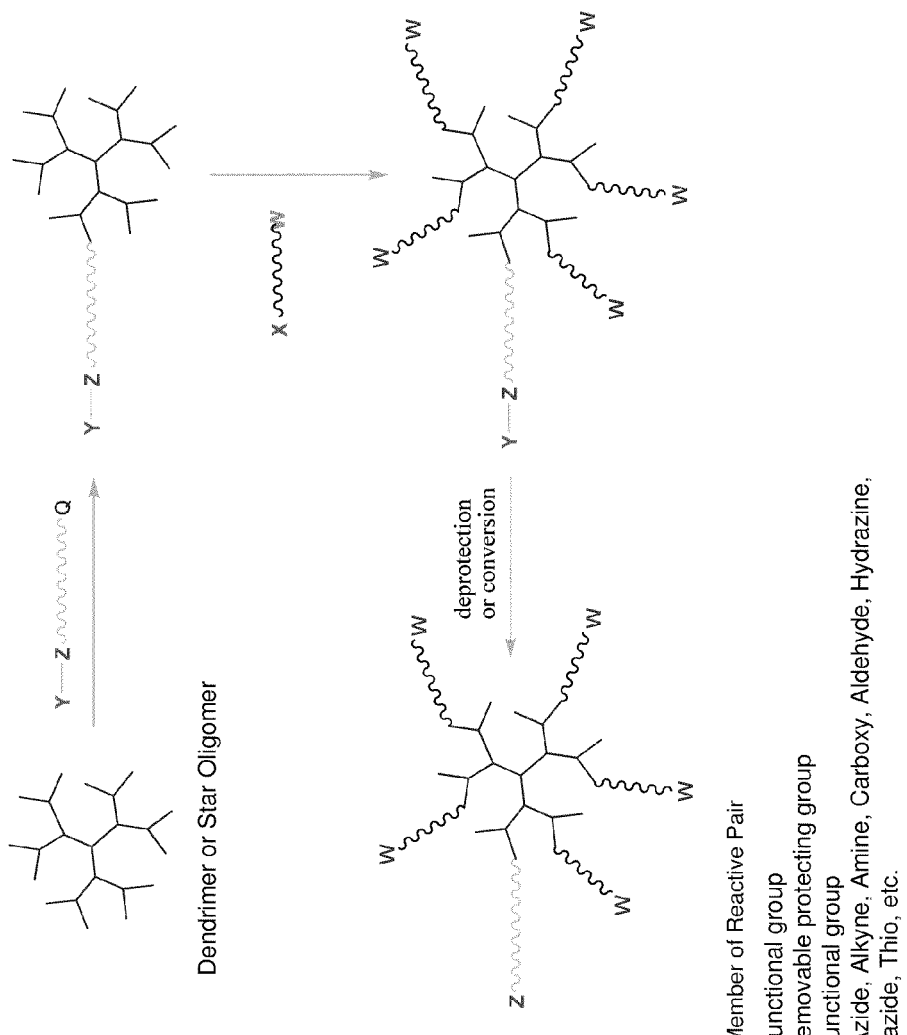
FIG. 12 illustrates the attachment of multiple first members of a reactive pair and the introduction of a coupling linker on dendrimer or star oligomer.

Linking molecules can also be synthesized by conjugating modified ODN to dendrimer or star oligomers comprising multiple first members of a reactive pair. FIGS. 11 and 12 together illustrate a two-step approach for the synthesis or modification of a dendrimer or star shape oligomer with multiple first members of a reactive pair followed by conjugation with a modified oligonucleotide. X and Z represent functional groups suitable for conjugation using, e.g., click chemistry, Thio and maleimide, thio and bromo-alkyl, aldehyde and hydrozine or hydrozide, amine and NHS ester, disulfide bond formation, Diels-Alder Reaction, etc.

Antibody Linking Molecules

In the context of protein targets, modified antibodies can be used as linking molecules. These linking molecules can be used to create multiple binding sites so as to enhance the efficiency and strength of binding to a relatively large entity, such as a substrate comprising a magnetic particle.

One example of an antibody linking molecule of interest is an antibody linking molecule which comprises one or more target-specific binding moieties specific for a target protein and which comprises one or more first members of a reactive pair.

Where a disclosed linking molecule comprises a plurality of target-specific binding moieties, this plurality can include, e.g., 2 or more, 3 or more, 4 or more, 5 or more, 6 or more, 7 or more, 8 or more, 9, or more, or 10 or more target-specific binding moieties.

Where a disclosed linking molecule comprises a plurality of first members of a reactive pair, this plurality can include e.g., 2 or more, 3 or more, 4 or more, 5 or more, 6 or more, 7 or more, 8 or more, 9, or more, or 10 or more first members of a reactive pair.

Figure 2B:
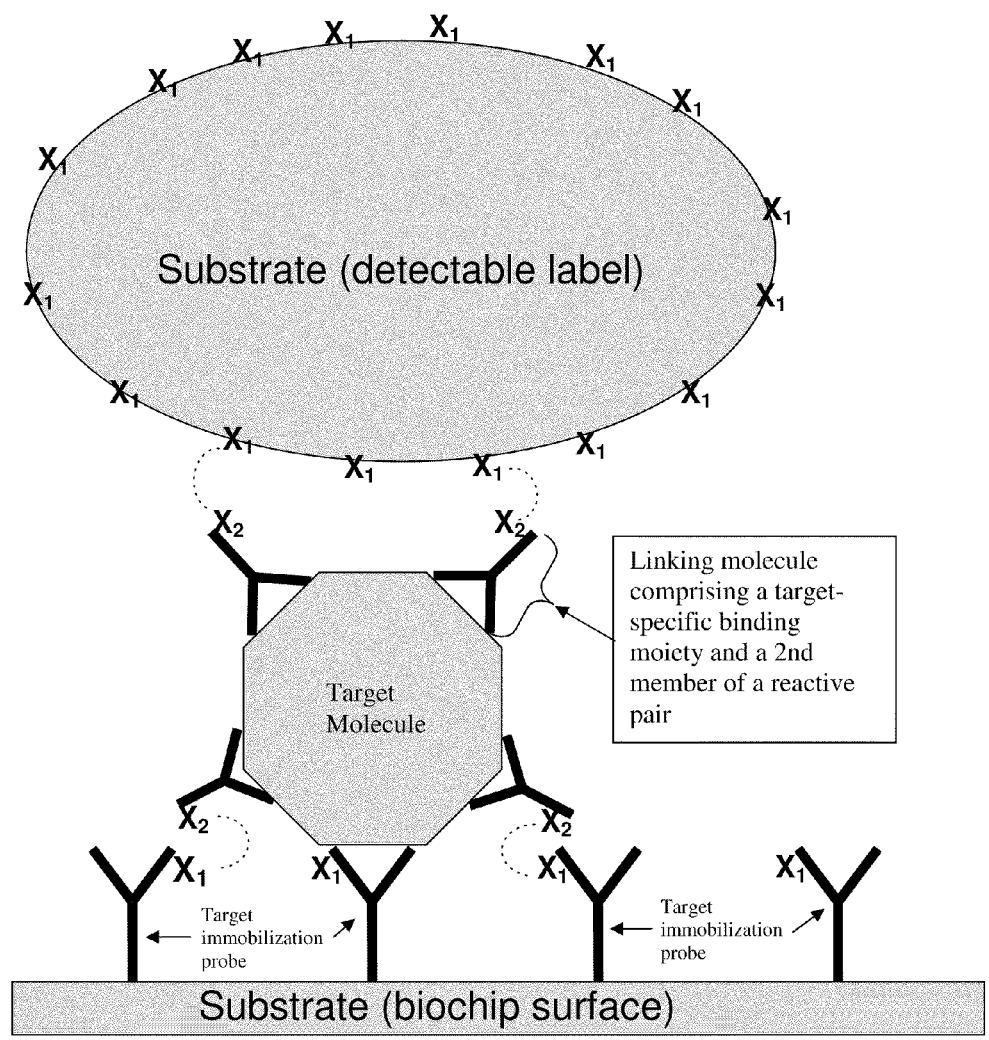
FIG. 2B provides an illustration of a binding complex comprising a target-immobilization probe, a non-nucleic acid target molecule (e.g., a protein or other biological entity), a plurality of linking molecules, a detectable label and a substrate comprising a biochip surface.
Figure 3:
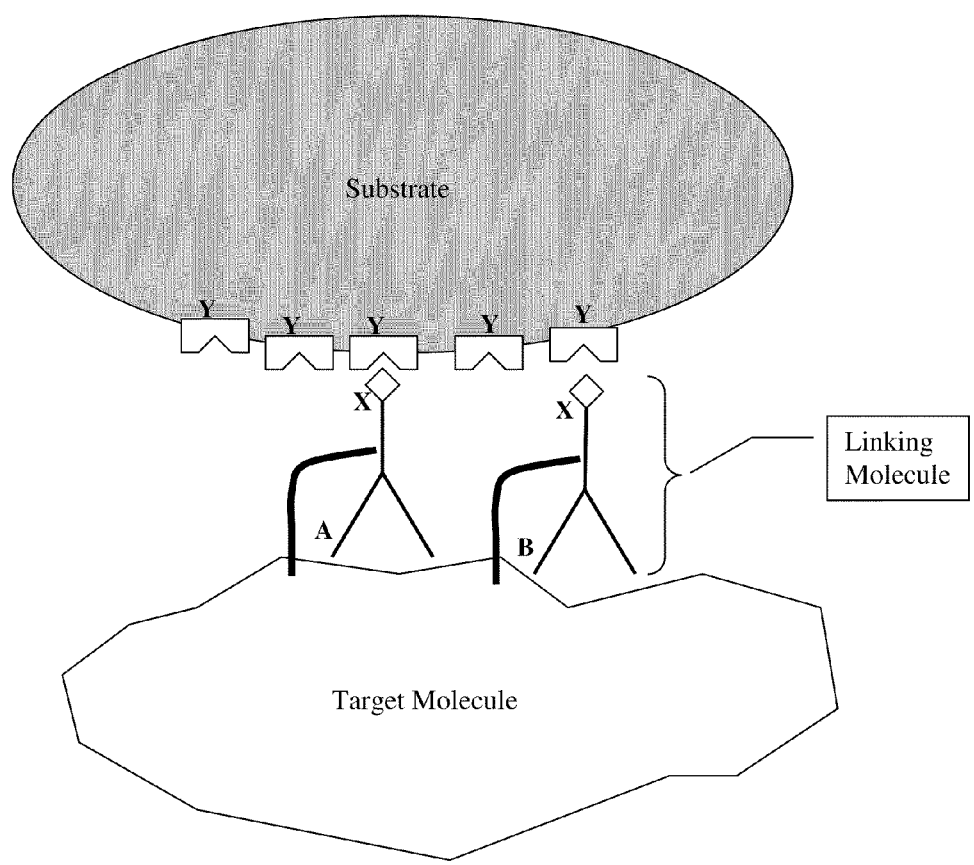
FIG. 3 provides an illustration of a binding complex comprising a polypeptide target molecule, a plurality of antibody based linking molecules and a substrate. X and Y represent 1$^{st}$ and 2$^{nd}$ members of a reactive pair respectively. A & B represent target-specific binding moieties capable of binding to different regions of the polypeptide target molecule. Optionally, an additional covalent cross linker can be applied to increase the strength of the binding complex.

In another example, a plurality of antibody linking molecules is disclosed, wherein each antibody linking molecule of the plurality of antibody linking molecules comprises a first member of a reactive pair and a target-specific binding moiety, wherein the target-specific binding moiety binds, under suitable conditions, to a different region of the target protein relative to the other members of the plurality. Illustrations of binding complexes formed by such linking molecules are provided in FIGS. 2B and 3.

Where a plurality of linking molecules is utilized, the plurality of linking molecules may be contacted to the target molecule (or a sample suspected of containing the target molecule) prior to contacting with the substrate so that the positioning of the linking molecules relative to the target molecule, prior to binding with the target molecule, is not significantly affected by the positions at which the linking molecules bind the substrate via members of a reactive pair.

The target-specific binding moiety or moieties of an antibody linking molecule can comprises a binding domain of an antibody or fragment thereof, e.g., an Fv region, capable of specifically binding to an epitope of a protein target molecule.

In one example, where a plurality of linking molecules are utilized, the epitopes bound by the target-specific binding moieties of the linking molecules are non-overlapping, such that each member of the plurality of antibody linking molecules is capable of binding to a different region of the protein target molecule.

In another antibody linking molecule example, a member of a specific binding pair can be bound to a carrier like bovine serum albumin or dendrimer. The carrier can then be bound to the antibodies specific for regions of the target molecule. This amplification cycle can be applied one or more times to produce linking molecules which provide the desired level of binding enhancement.

Specific binding pairs of interest include, e.g., polypeptides and various haptens (such as fluorescene or digoxigen) recognized by specific antibodies, ligands for binding receptors, biotin for strepavidin or avidin and oligonucleotides for hybridization with complementary sequences.

In particular embodiments, the linking molecules utilized in the disclosed methods and compositions bind or react with a moiety added to a protein during post-translational modification of the protein. For example, in some embodiments the disclosed linking molecules bind or react with a glycosyl group or a carbohydrate added to a protein during post-translational modification. In other embodiments, the linking molecules utilized in the disclosed methods and compositions do not bind or react with a moiety added to a protein during post-translational modification of the protein. For example, in some embodiments the disclosed linking molecules do not bind or react with a glycosyl group or a carbohydrate added to a protein during post-translational modification.

Preparation of Antibody Linking Molecules

A variety of techniques are known in the art which can be utilized in the preparation of the antibody linking molecules disclosed herein. See, for example, Harlow, E. & Lane, D. 1998. *Antibodies: A Laboratory Manual*. New York: Cold Spring Harbor Laboratory Press, for general methods of antibody preparation and labeling.

In addition, methods of incorporating specific binding pair members and reactive pair members into polypeptides are known in the art. For methods of labeling of antibodies with biotin see Harlow, E. & Lane, D. 1998. *Antibodies: A Laboratory Manual*. New York: Cold Spring Harbor Laboratory Press. For the incorporation of azide/alkyne binding pair members into polypeptides, see Wang, Q. et al. (2003) *J. Am. Chem. Soc.* 125: 3192-3193, incorporated herein by reference. For more general methods of protein modification and conjugation, see Greg T. Hermanson Bioconjugate Techniques, published by Academic Press 1996.

Suitable conditions for antibody binding are also well known in the art. See, e.g., Harlow and Lane (Using Antibodies: A Laboratory Manual, CSHL Press, 1999); Harlow et al. (*Antibodies: A Laboratory Manual*, First Edition (1988) Cold spring Harbor, N.Y. Harlow, Sambrook and Ausubel, supra); Sambrook, et al, (Molecular Cloning: A Laboratory Manual, Third Edition, (2001) Cold Spring Harbor, N.Y.); and Ausubel, et al, (Short Protocols in Molecular Biology, 3rd ed., Wiley & Sons, 1995).

Label Probes

In some embodiments described herein, label probes are utilized to non-covalently bind a detectable label to a target molecule of interest. Label probes are molecules coupled to a detectable label, wherein the molecule is capable of binding specifically and at least non-covalently to a target molecule when brought into contact with the target molecule under suitable conditions. Where such label probes comprise nucleic acid sequences, such probes are typically from about 10 to about 80 bases in length. For example, the nucleic acid molecules conjugated to the particle labels can be about 10 to about 20, about 20 to about 30, about 30 to about 40, about 40 to about 50, about 50 to about 60, about 60 to about 70, or about 70 to about 80 nucleotides in length. More typically, the nucleic acid molecules conjugated to the particle labels are about 10 to about 60 nucleotides in length, even more typically about 10 to about 45 nucleotides in length.

Detectable Labels

There are a variety of detectable labels known in the art which can be utilized in connection with the disclosed methods and compositions. These include e.g, radioactive isotopes, fluorescers, chemiluminescers, chromophores, enzymes, enzyme substrates, enzyme cofactors, enzyme inhibitors, metal ions, magnetic particles, members of a specific binding pair and the like.

Detectable labels may be in the form of particles, e.g., microparticles or nanoparticles. Where a magnetic particle is utilized in the methods and/or compositions disclosed herein, the magnetic particle can be, e.g., a magnetic nanoparticle or micro-particle. Magnetic particles include, for example, magnetic beads or other small objects made from a magnetic material such as a ferromagnetic material, a ferrimagnetic material, a paramagnetic material, or a superparamagnetic material. In some embodiments, the magnetic particles comprise iron oxide ($Fe_2O_3$ and/or $Fe_3O_4$) with diameters ranging from about 10 nanometers to about 100 micrometers. Magnetic nanoparticles are available, for example, from Miltenyi Biotec Corporation of Bergisch Gladbach, Germany. These are relatively small particles made from coated single-domain iron oxide particles, typically in the range of about 5 to about 500 nanometers diameter. Magnetic particles can also be made from magnetic nanoparticles embedded in a polymer matrix such as polystyrene. These are typically smooth and generally spherical having diameters of about 0.2 to about 5 micrometers. Particles of this type are available from Invitrogen Corporation, Carlsbad, Calif. Additional examples of magnetic particles include those described by Baselt et al. (1998) *Biosensors & Bioelectronics* 13: 731-739, Edelstein et al. (2000) *Biosensors & Bioelectronics* 14: 805-813, Miller et al. (2001) *J. of Magnetism and Magnetic Materials* 225: 138-144, Graham et al. (2002) *J. Appl. Phys.* 91: 7786-7788, Ferreira et al. (2003) *J. Appl. Phys.* 93, pp. 7281-7286, and U.S. Patent Application Publication No. 2005/0100930 (published May 12, 2005).

In one aspect, magnetic particles having an average diameter of about 10 nanometers to about 1000 nanometers are utilized in the disclosed methods and compositions, e.g., magnetic particles having an average diameter of about 100 nm to about 900 nm, about 200 nm to about 800 nm, about 300 nm to about 700 nm, about 400 nm to about 600 nm, or about 500 nm.

Cross-Linking to Strengthen and/or Stabilize a Binding Complex

The strength and/or stability of a binding complex can be increased by cross-linking and through the introduction of high-strength covalent bonds. These techniques can be utilized alone or in combination with the linking molecules described herein to provide strong, stable target molecule-substrate binding complexes, e.g., target molecule-detectable label complexes and/or target molecule-biochip surface binding complexes.

For example, a binding interaction between two or more of the binding entities found in a single target molecule-substrate binding complex can be strengthened and/or stabilized by the introduction of one or more cross-linking agents. This type of cross-linking can be described as "intra-complex cross-linking." In some embodiments, this "intra-complex cross-linking" involves the introduction of covalent bonds into an intramolecular complex. It may be desirable, for example, to stabilize a target bound to a biochip surface via one or more linking molecules prior to contacting with a substrate comprising a detectable label. In some embodiments, it may be desirable to further stabilize the binding complex after a detectable label has bound to the target molecule via one or more linking molecules.

The disclosure also contemplates the use of cross-linking agents to introduce "inter-complex cross-linking." For example, in one embodiment a single complex can be described by the following formula A-B-C-D, wherein A=a biochip surface comprising a plurality of target-immobilization probes, B=a target molecule, C=one or more linking molecules, and D=a detectable label. This single complex can be linked to one or more additional complexes present on a substrate surface through the introduction of cross-linking agents.

Cross-Linking Through the Introduction of Covalent Bonds

Cross-linking agents can be introduced to facilitate the formation of covalent bonds between members of a binding complex and/or between complexes. Covalent bonds are usually in the range of 300-400 kJ/mol. These bonds are many folds stronger than the non-covalent binding interaction between a receptor and its ligand, protein and protein or hybridized double stranded nucleic acids.

Figure 4:
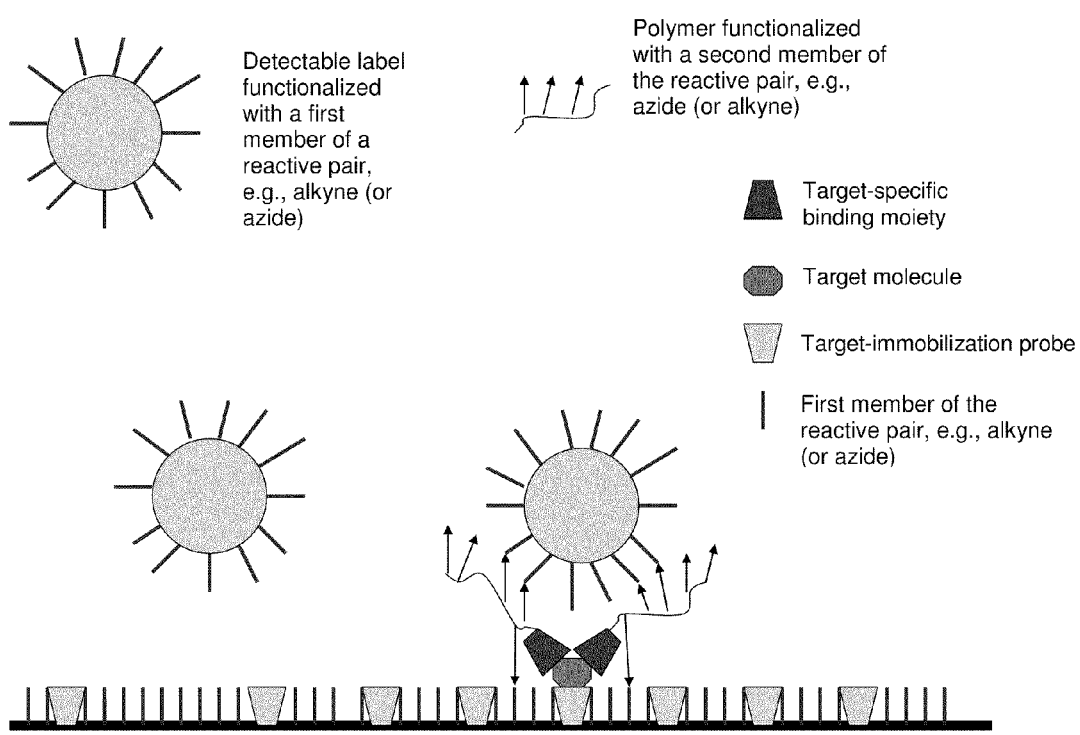
FIG. 4 provides an illustration of a binding complex comprising a target-immbolization probe, a target molecule, a linking molecule, a detectable label, and a substrate comprising a biochip surface. The detectable label is functionalized with a first member of a reactive pair, e.g., an alkyne (or azide). The linking molecule comprises a target specific binding moiety and a polymer functionalized with second members of the reactive pair, e.g., azide (or alkyne). The substrate comprising the biochip surface is also functionalized with first members of the reactive pair. This configuration allows for the formation of covalent bonds between the linking molecule and the detectable label and between the linking molecule and the substrate comprising the biochip surface.

By way of example, each of FIGS. 2 and 4 show exemplary embodiments involving the use of cross-linking agents to introduce additional covalent bonds in the disclosed binding complexes. In these examples, members of reactive pairs are utilized not only to form covalent bonds between linking molecules and detectable labels, but also to form covalent bonds between linking molecules and members of the reactive pair present on a biochip surface.

While FIGS. 2 and 4 demonstrate cross-linking with respect to particular linking molecule embodiments, it is to be understood that such cross-linking may be applied to complexes comprising any of the linking molecule embodiments disclosed herein.

A variety of covalent bond forming binding pair interactions are known in the art including Cu-catalyzed azide/alkyne [3+2] cycloaddition "click chemistry," azide/DIFO (Difluorinated Cyclooctyne) Cu-free click chemistry, azide/phosphine "Staudinger Reaction," azide/triarylphosphine "Modified Staudinger Reaction," and catalyzed olefin cross metathesis reactions. These binding pair reactions may be utilized to introduce covalent bonds to stabilize and/or strengthen the interactions between members of a (target)-(linking molecule)-(substrate) binding complex. Those of skill in the art will understand that some of these reactions, e.g., Cu-catalyzed azide/alkyne [3+2] cycloaddition, require the addition of a catalyst agent to catalyze the binding pair interaction, while other such as the azide/DIFO reaction do not.

Figure 5:
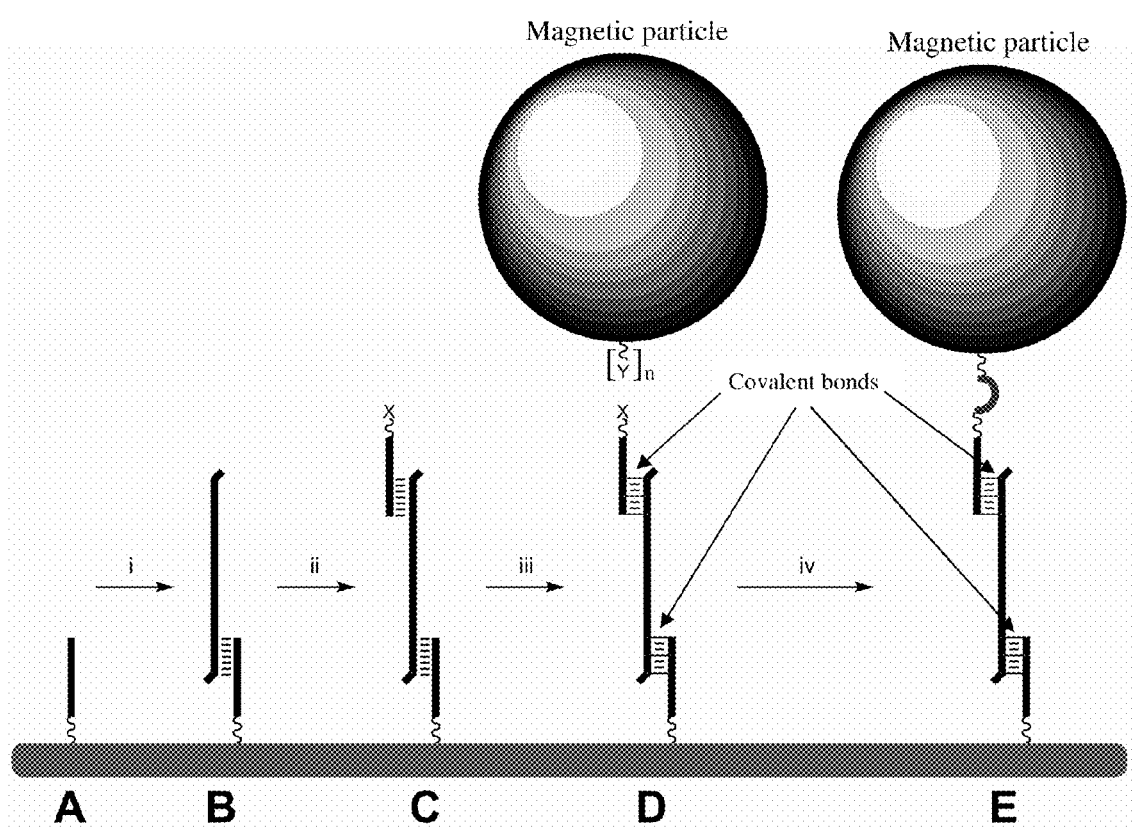
FIG. 5 illustrates the use of linking molecules comprising members of a reactive pair to covalently "fix" a nucleic acid detection structure between a MTJ array biochip surface and a magnetic particle. X and Y represent first and second members of a reactive pair respectively. (i) Target nucleic acid hybridizes specifically to a target-immobilization probe (A) on the biochip surface (B). (ii) A linking molecule with a first member of a reactive pair X is hybridized to the captured target nucleic acid molecule (C). (iii) The non-covalent structure is covalently "fixed" (D) with a nucleic acid cross linking agent, e.g., psoralen. (iv) The covalent structure (D) is incubated with magnetic particles functionalized with a second member of the reactive pair Y that is capable of forming a covalent bond with X to generate a completely covalently "fixed" structure (E). The presence of the magnetic particles is subsequently detected by the MTJ sensor array. "n" indicates a plurality of the bracketed members.

FIG. 5 illustrates an exemplary embodiment in which the introduction of cross-linking agents results in the formation of covalent bonds between hybridized nucleic acid strands. There are a variety of agents available in the art which can be used to crosslink between strands of hybridized nucleic acids, between nucleic acids and proteins, and between different protein molecules. Cross-linking agents of different lengths and combinations of functional groups are available commercially.

For example, psoralens, a class of photo mutagenic compounds that form covalent nucleic acid adducts through photochemical addition, can be utilized. The primary reaction is cyclobutane ring formation between the 5,6 double bond of thymidine in DNA and either the 4',5' or 3,4 double bond of the psoralen. Reaction at the 4',5' double bond creates a furan-side monoadduct, which can further react at a site with a flanking pyrimidine on the opposite strand to create an interstrand cross-link. Spielmann et al. (1995) *Proc. Natl. Acad. Sci.* USA Vol. 92, pp. 2345-2349. See also, Okamoto et al. (2001) Org. Lett. March 22; 3(6):925-7, describing the synthesis of a psoralan containing peptide nucleic acid (PNA) from 8-methoxypsoralen. PNA containing a psoralen unit at strand end forms a stable duplex with complementary DNA. Psoralen's with additional functionality have also been synthesized. For example, Saffran et al. (1988) *Nucleic Acids Research;* 16(15):7221-31, describe the synthesis of a biotinylated psoralen (BPsor). BPsor photoreacts with DNA to form interstrand cross-links while providing an additional binding functionality in the form of the attached biotin which can then interact with a streptavidin molecule.

Crosslinking of hybridized nucleic acid molecules can also be accomplished as described in U.S. Pat. No. 6,800,768 (issued Oct. 5, 2004), wherein non-nucleosidic photoactive coumarin derivatives are incorporated into nucleic acids to facilitate cros slinking.

Alternatively, cross-linking agents can be designed and synthesized to fit the requirements of a particular cross-linking situation.

As described in Pendergrast et al. (1992) *Proc. Nati. Acad. Sci.* USA Vol. 89, pp. 10287-10291, photocrosslinking can also be utilized to stabilize binding interactions between proteins and nucleic acids. Specifically, Pedergrast et al. incorporate a photoactivatable crosslinking agent at a single amino acid within a protein by a two-step procedure consisting of site-directed mutagenesis followed by cysteine-specific chemical modification. First, site-directed mutagenesis is used to introduce a unique solvent accessible cysteine residue at the position of interest. Then, one derivatizes the resulting protein with a cysteine specific heterobifunctional photoactivatable crosslinking agent, e.g., 4-azidophenacyl bromide. Under defined conditions, reaction of 4-azidophenacylbromide with a protein having a unique solvent-accessible cysteine residue results in complete and highly selective derivatization of the cysteine residue to yield a conjugate of the form [(4-azidophenacyl)-Cys]protein. One then forms the protein-DNA complex and UV irradiates the protein-DNA complex to introduce cros slinking.

The cros slinking agents can be applied as separate and independent reagents.

Alternatively, cross linking functional groups can be directly conjugated to the linking molecules, target immobilization probes, substrates, etc. The functional group can be activated on command by input such as light, pH changes or specific chemicals applied at a desired point in time. Additionally, the binding moieties and/or linking molecules disclosed herein can be designed to make them suitable for the application of cros slinking agents of choice. For example, conjugating protein or other chemical entities to target-specific binding moieties comprising nucleic acids makes it possible to broaden the selection of cross linking agents to those originally not applicable for nucleic acids.

Introduction of Complementary Nucleic Acids

Complementary nucleic acid sequences can be introduced to enhance the strength of binding between binding complexes since the binding strength between a pair of hybridized strands can be designed to exceed that of most non-covalent binding pairs such as antibody-antigen binding pairs. For example, nucleic acids with a chosen sequence can be conjugated to linking molecules such as antibody linking molecules. A molecule comprising regions of nucleic acid complementarity to the sequences conjugated to two or more linking molecules can then be utilized to produce inter-complex and/or intra-complex cross-linking. Such nucleic acids can be designed to be of appropriate length to ensure proper hybridization. This can be achieved by inserting a linker section of desired length in the bridging nucleic acid. The linker section can comprise any suitable substance including nucleotides and other polymers such as polyethylene glycol.

Methods of Creating a Target Molecule-Substrate Complex Having Multiple Intra-Complex Binding Interaction Sites The linking molecules described herein find use in methods designed to create a target-substrate complex having multiple intra-complex binding interaction sites. These methods can be used, for example, in connection with assays designed to determine the presence or absence of a particular target molecule in a sample. The disclosed methods can also be used to determine quantitatively the amount of a particular target molecule in a particular sample. Generally, the methods described herein involve combining in a reaction mixture a sample suspected of containing a target molecule, one or more functionalized substrates and one or more linking molecules as described herein.

In one embodiment, the method utilizes two distinct types of substrates. The first type comprises a biochip surface, and the second type is a detectable label or is modified to include a detectable label. A sample suspected of containing a target molecule is combined in a reaction mixture with one or more linking molecules described herein. After allowing a sufficient amount of time for the linking molecules to bind to the target molecule if present, the reaction mixture is contacted with a substrate comprising a biochip surface as described herein. The biochip surface can be functionalized with one or more target immobilization probes. Where target immobilization probes are utilized, the (target molecule)-(linking molecule) complex, can be directly bound by the target immobilization probes. The reaction mixture can then be contacted with the second type of substrate, i.e., the detectable label. Members of a reactive pair present on the detectable label allow for binding to the one or more linking molecules bound to the target molecule. In this manner, an immobilized complex comprising the target molecule and the detectable label is formed. The presence and/or quantity of the detectable label can then be detected according to a variety of methods known in the art, e.g., through the use of a magnetic sensor incorporated into a biochip.

In some embodiments, one or more of the above binding steps are followed by one or more wash steps to remove non-specifically bound molecules.

It should be noted that although some embodiments utilize a target immobilization probe to immobilize the target molecule on the biochip surface, immobilization of the target molecule on the biochip surface can also be accomplished using one or more linking molecules in combination with one or more members of a reactive pair bound to the biochip surface. As such, in some embodiments the disclosed methods result in the formation of a binding complex, wherein a target molecule is bound to a biochip surface via one or more linking molecules which bind to members of a reactive pair on the biochip surface, and wherein a detectable label is bound to the target molecule via one or more linking molecules which bind to members of a reactive pair on a detectable label.

Introducing Covalent Binding Interactions between a Target Molecule and a Substrate to Produce a Detectable Covalent Binding Complex The introduction of covalent bonds using cross-linking agents, e.g., psoralens, and/or members of a reactive pair, e.g., azide/alkyne [3+2] cycloaddition "click chemistry," can be used to increase the strength of binding interactions between target molecules and substrates. These techniques can be utilized alone or in combination with the linking molecules described herein to produce stabilized binding complexes comprising detectable labels, target molecules and biochip substrates.

For example, click chemistry can be utilized wholly or in part to produce a robust covalently linked structure to enhance particle-based detection of target molecules. FIG. 5 illustrates the formation of a binding complex using a target-immobilization probe, a linking molecule and a detectable label exemplified by a magnetic particle to capture and label a target nucleic acid sequence. While FIG. 5 depicts the formation of a complex comprising a nucleic acid target molecule, it should be noted that the general method steps are equally applicable to other targets, e.g., protein targets. Two types of covalent "fixing" of the structure are shown. These types of covalent "fixing" can be used alone or in combination.

In the exemplary embodiment shown in FIG. 5, a nucleic acid target molecule is hybridized with a target-immobilization probe on a biochip surface, followed by hybridization of a linking molecule The linking molecule comprises a first member of a reactive pair, e.g., a click chemistry functional group, denoted X, and a nucleic acid sequence capable of hybridizing specifically with the target molecule. A wash step can be performed to remove linking molecules not specifically hybridized to the target. The structure can be incubated with magnetic particles functionalized with a second member of the reactive pair (denoted Y) capable of reacting with the first member of the reactive pair to complete the covalent "fixing" of the nucleic acid detection structure between the biochip surface and the magnetic particle. Where the reaction of the members of the reactive pair requires the addition of a catalyst, e.g., in azide/alkyne [3+2] cycloaddition, a suitable catalyst (e.g., Cu ion) is included. Alternatively, reactions such as the azide/DIFO reaction may be utilized to covalently link the magnetic particle and the linking molecule in the absence of added catalyst. The resulting covalent binding complex can be detected using any suitable magnetic sensor, e.g., a magnetic tunnel junction (MTJ) sensor. As illustrated in FIG. 5, the resulting non-covalent structure can be cross-linked with a nucleic acid-cross linking agent, e.g., psoralen. Many cross linking agents are known in the art for both proteins and nucleic acids, such as those commercially available from Pierce Biotechnology, Inc. and Fisher Scientific International. Additional cross linking agents can be custom synthesized. While FIG. 5 shows this step as occurring prior to formation of a covalent bond between first and second members of the reactive pair, this step can be performed at any suitable time during the process, e.g., after formation of a covalent bond between first and second members of the reactive pair.

Figure 6:
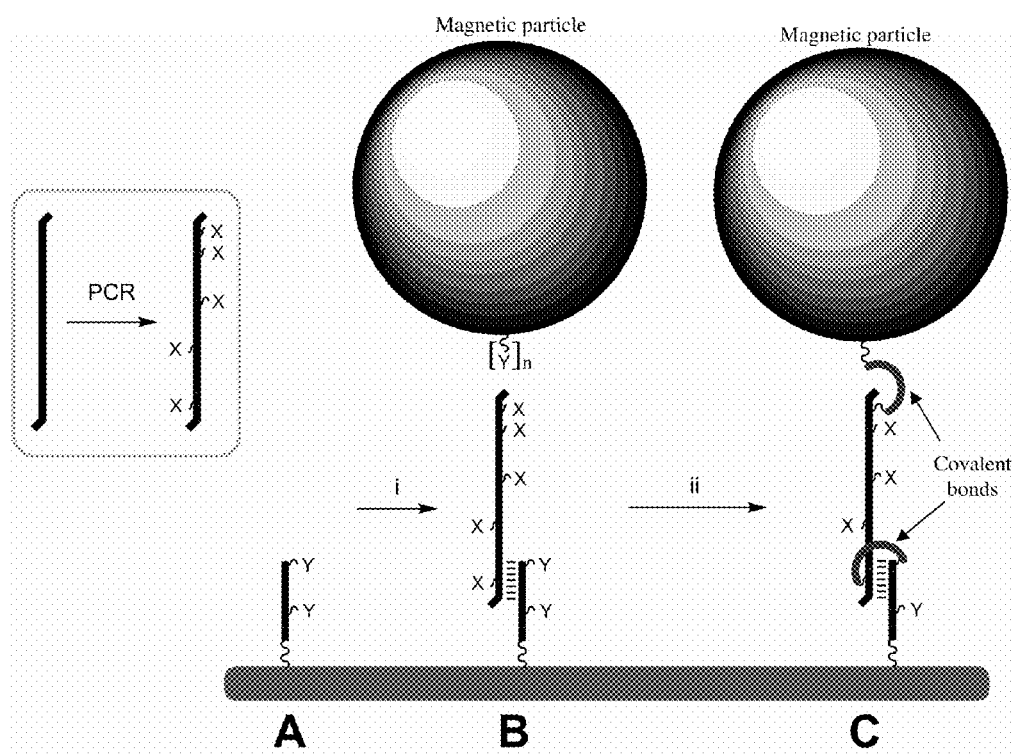
FIG. 6 illustrates the use of linking molecules comprising members of a reactive pair to covalently "fix" a nucleic acid detection structure between a MTJ array biochip surface and a magnetic particle. X and Y represent first and second members of a reactive pair respectively.

FIG. 6 shows an embodiment in which the magnetic particle is functionalized with a member of a reactive pair, denoted Y. In the specific example shown in FIG. 6, a nucleic acid target molecule is amplified using PCR. In the reaction mixture, one or more of the standard deoxynucleotide triphosphates (dNTPs) are replaced with a dNTP modified to introduce a first member of the reactive pair. As a result, the amplicon has one or more bases modified to include the first member of the reactive pair, denoted X.

The amplicon can be hybridized to a target-immobilization probe on the surface of a biochip. The target immobilization probe can also be modified to contain a second member of the reactive pair, denoted Y, which, under suitable conditions, is capable of forming a covalent bond with a first member of the reactive pair present in the amplicon. The non-covalent structure formed via hybridization can be incubated with magnetic particles functionalized with second members of the reactive pair, wherein the incubation is under conditions suitable for the formation of covalent bonds between first and second members of the reactive pair. For example, where the first and second members of the reactive pair are click chemistry function groups, the incubation may take place in the presence of a Cu ion catalyst.

The non-covalent structure formed via hybridization of the target-immobilization probe to the modified target molecule can be cross-linked with a nucleic acid-cross linking agent, e.g., psoralen. This step can be performed at any suitable time during the process, e.g., before or after formation of a covalent bond between first and second members of the reactive pair.

Figure 7:
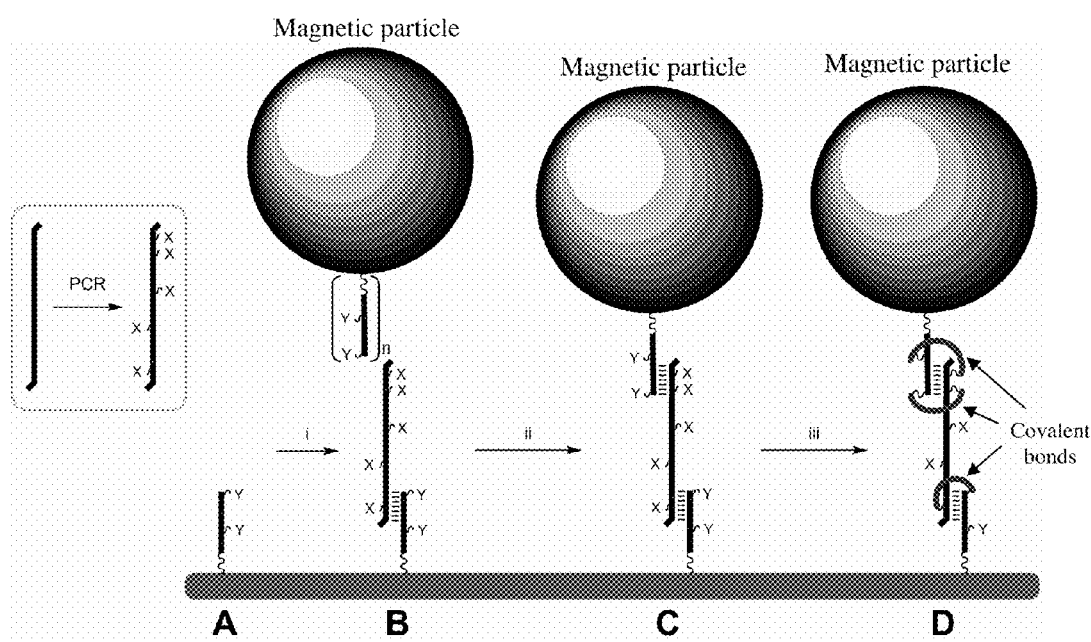
FIG. 7 illustrates an alternative strategy for the utilization of reactive pairs to covalently "fix" a nucleic acid detection structure between a MTJ array biochip surface and a magnetic particle. Unlike the strategy illustrated in FIG. 6, the strategy illustrated in FIG. 7 describes an approach which does not utilize a label probe. Instead, a first member of the reactive pair forms a covalent bond with a second member of the reactive pair conjugated to the magnetic particle. A covalent bond is also formed between the modified target molecule and the functionalized target-immobilization probe. Target nucleic acid is amplified via PCR with a modified base to introduce first members of a reactive pair, denoted X, into the resultant amplicon (inset). (i) The modified amplicon hybridizes specifically to a target immobilization probe on the biochip surface. The target-immobilization probe (A) is modified with one or more second member of said reactive pair, denoted Y, that are capable of forming covalent bonds with the first members of the reactive pair. (ii) The non-covalent structure (B) is incubated with magnetic beads functionalized with a label probe modified with second members of the reactive group Y to complete the non-covalent nucleic acid detection structure (C). (iii) Under suitable conditions, covalent bonds are formed as shown to covalently "fix" the structure (D). The presence of magnetic particles is subsequently detected by the MTJ sensor array. "n" indicates a plurality of the bracketed members.

A further embodiment is illustrated in FIG. 7. Where the target of interest is a nucleic acid, the nucleic acid target molecule can be amplified using PCR. In the reaction mixture, one or more of the standard deoxynucleotide triphosphates (dNTPs) are replaced with a dNTP modified to introduce first members of a reactive pair, e.g., a click chemistry functional group. As a result, the amplicon has one or more bases modified to include first members of the reactive pair, denoted X. The amplicon can then be hybridized to a target-immobilization probe on the surface of a biochip. The target immobilization probe is modified to contain a second member of the reactive pair, denoted Y, which, under suitable conditions, is capable of forming a covalent bond with a first member of the reactive pair present in the amplicon. The non-covalent structure formed via hybridization can then be incubated with magnetic particles functionalized with a labeling probe. Where the target is a nucleic acid, the labeling probe comprises a nucleic acid sequence capable of hybridizing specifically with a sequence of the amplicon. The labeling probe also comprises a second member of the reactive pair, which, under suitable conditions, is capable of forming a covalent bond with first member of the reactive pair in the amplicon. Hybridization of the labeling probe with the amplicon completes a non-covalent nucleic acid binding complex. When the reaction conditions require the use of a catalyst, such a catalyst is added to covalently "fix" the nucleic acid detection structure between the biochip surface and the magnetic particle thereby producing a detectable covalent binding complex. The resulting covalent binding complex can be detected using a magnetic sensor. It is also contemplated that psorlan or another suitable nucleic acid crosslinking agent could be used in connection with this method to introduce additional covalent bonds thereby further stabilizing the detectable covalent binding complex.

As discussed previously herein, methods of modifying nucleic acids with click chemistry azide/alkyne reactive pair members are known in the art. See, for example, Salic and Mitchison (2008) *PNAS* 105 (7): 2415-2420, describing the incorporation of 5-ethynyl-2'-deoxyuridine (EdU) and its subsequent detection by a fluorescent azide through a Cu-catalyzed [3+2] cycloaddition reaction, which is incorporated by reference herein. See also, WO 2008/052775, published May 8, 2008, describing the synthesis of nucleotide building blocks modified with click chemistry functional groups, which is incorporated by reference herein. These methods can be utilized in connection with the methods described herein for producing detectable covalent binding complexes.

EXAMPLES

Example 1

Synthesis of Branched or Dendrimer Molecule Comprising First Members of a Reactive Pair and Conjugation with Oligo-Deoxynucleotide (ODN) as Target Binding Moiety As indicated above, FIGS. 8-12 illustrate synthesis schemes for various "branched" and "star" linking molecules comprising an oligodeoxynucleotide (ODN) target-specific binding moiety and multiple first members of a reactive pair.

Two exemplary synthesis approaches are described in the following prophetic example. Both approaches employ solid phase oligonucleotide synthesis chemistry schemes with variations such as applying monomers for solid surface synthesis of different sizes and functional groups to produce the desired spacing and chemistry. One approach is to synthesize the oligonucleotide sequence for binding to the nucleic acid target and the branched moiety with first reactive pair members as a whole on the solid support as depicted in FIG. 8. Alternatively, the branched moieties and the target binding moieties are synthesized separately and then conjugated to form the whole molecule afterwards as depicted in FIGS. 9 and 10.

In both approaches, controlled pore glass (CPG) with a cleavable protecting group DMT (dimethoxytrityl) on solid support is used to start the solid phase synthesis. After removing the DMT group with acid solution, if the approach is to directly synthesize the entire linking molecule, oligonucleic acid synthesis is performed first to generate a stretch of target binding oligonucleotide before starting the synthesis of the branched moieties, as depicted in FIG. 8. If the approach is to synthesize the two parts separately and then conjugate them together, as depicted in FIGS. 9 and 10, the synthesis of the branched or star moiety on the solid surface can start right away on the solid support.

A unit of "Y" shaped bifunctional linker is coupled onto the solid support using phosphoramidite synthesis chemistry. As depicted in FIG. 9 the "Y" shaped bifunctional linker has at the ends of its two symmetrical arms, two functional groups capped by protecting groups X, such as DMT. The DMT groups can be deblocked using acidic solution, and then another unit of the "Y" shaped bifunctional linker can be incorporated. After a desired number of units of "Y" shaped bifunctional linker are incorporated into the backbone, the DMT groups can be deblocked using acidic solution. After the removal of the protection group such as DMT, the exposed hydroxyl groups can be modified to generate several functional groups of choice. For example, an alkynyl functional group can be introduced on these terminal hydroxyl groups using 5'-hexynyl phosphoramidite. At the completion of the synthesis, the whole branched linker molecule can be cleaved from the CPG solid support by strong alkaline solution. The final compound can be used to produce complexes comprising target molecules and detectable magnetic particles on a MTJ biosensor.

Example 2

Synthesis of Multiple First Members of a Reactive Pair on a Dendrimer Molecule and Conjugation with Oligo-deoxynucleotide (ODN) as Target Binding Moiety A prophetic example of a linking molecule synthesis scheme utilizing dendrimers is as follows:

Polyamidoamine (PAMAM) dendrimers of various generations (sizes) with a cystamine core and terminal amino groups on the dendrions are commercially available from Dendritic Nanotechnologies Inc. (Dendritic Nanotechnologies, Inc., 2625 Denison Drive. Mount Pleasant, Mich. 48858). The terminal amino groups can be readily derivatized to add covalent bond forming reactive pair members by using various modification or cross linking reagents which are available commercially from Sigma-Aldrich or Pierce Biotechnology in Thermo Fisher Scientific. For example, the terminal amino groups can be converted to alkynyl groups by reaction with hexynoic acid activated by a carbodiimide reagent such as EDC. The terminal amino groups can also be converted to azido groups by first modifying the amino groups with succinnic anhydride. The resulting terminal carboxyl groups can be activated by EDC and conjugated with 1-Amino-11-azido-3,6,9-trioxaundecane which is available from Sigma-Aldrich.

Either before or after the modification of the terminal amino groups, which results in the formation of multiple first members of a reactive pair, the dendrimers with cystamine core can be reduced to sulfhydryl groups which provide a unique site to allow the conjugation of various target-specific binding moieties. Conjugation of the functionalized dendritic molecule with a free sulfahydryl group to a protein, peptide or nucleic acid target-specific binding moiety usually requires the use of a heterobifunctional cross linker such as succinimidyl 4-[N-maleimidomethyl]cyclohexane-1-carboxylate. Optionally the conjugation can be mediated through a spacer to provide adequate spacing and minimize steric hindrance.

In this way, a linking molecule comprising a target-specific binding moiety and multiple first members of a reactive pair can be synthesized.

Example 3

"Two-step" Synthesis Scheme for a Branched Linking Molecule

In order to synthesize a branched linking molecule the following prophetic synthesis scheme utilizing phosphoramidite chemistry on a solid support can be performed.

Figure 13:
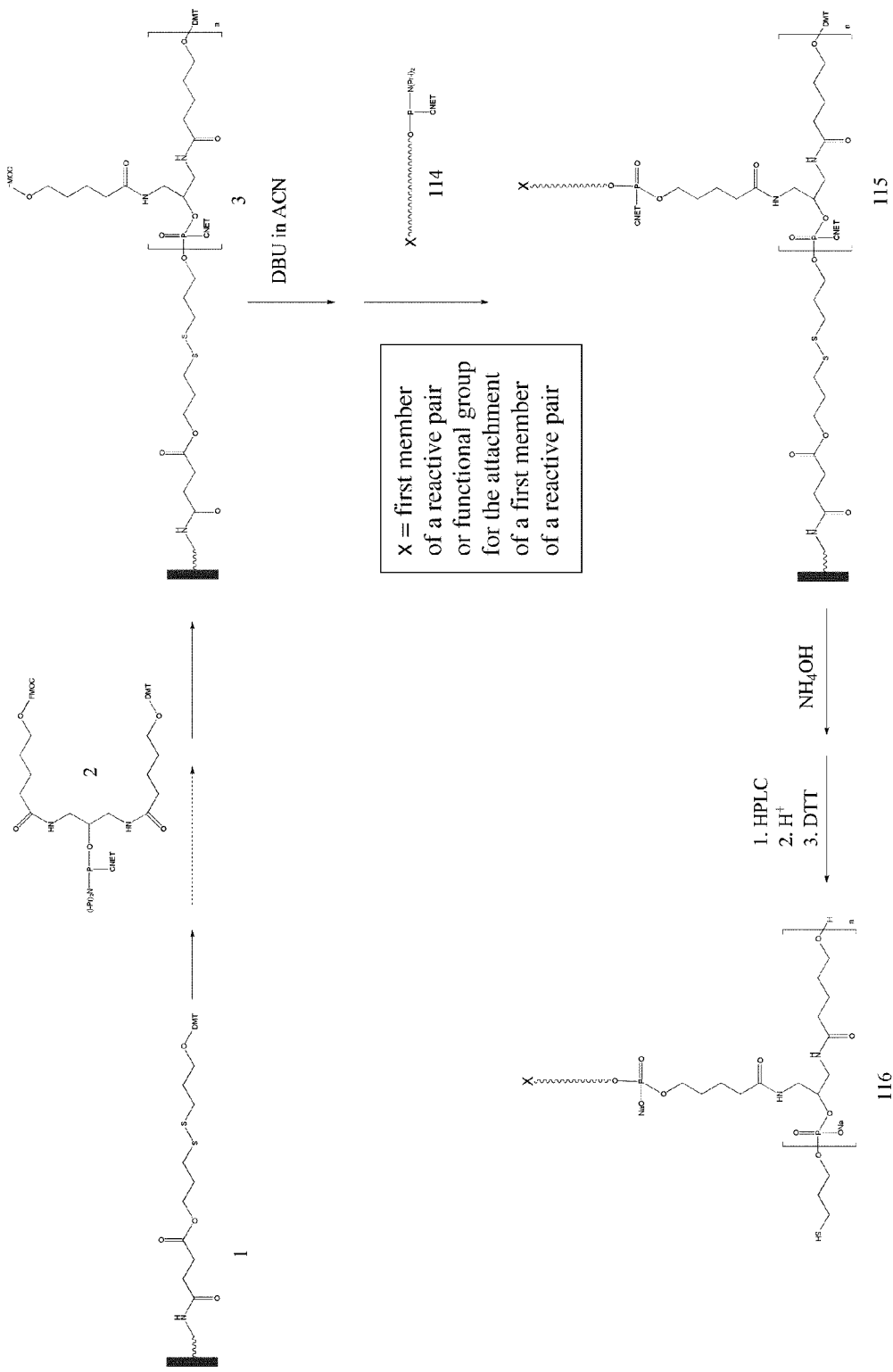
FIG. 13 illustrates a synthesis scheme using phosphoramidite chemistry with various monomers X for the synthesis of a branched moiety comprising multiple first members of a reactive pair.

As indicated in FIG. 13, controlled pore glasses beads (CPG) derivatized with a cleavable monomer (1), are used as solid support to start the synthesis. After removing the protecting group DMT (dimethoxytrityl) with acid solution a hydroxyl group is exposed. A unit of "Y" shaped bifunctional monomer (2) is coupled to monomer (1) using phosphoramidite chemistry. The "Y" shaped bifunctional monomer (2), called asymmetric doubler phophoramidite, has two different protecting groups at each terminal: DMT, an acid labile group, and FMOC, a base labile group. The DMT group can be removed again using acidic solution, and then another unit of the "Y" shaped bifunctional monomer (2) is incorporated to extend the backbone of the branched entity.

Multiple units of the "Y" shaped bifunctional monomers can be incorporated by repeating the same phosphoramidite chemistry. The FMOC protecting groups are stable during the multiple iterations of the coupling reactions. After the desired number of units of "Y" shape bifunctional monomer is incorporated into the backbone, the FMOC protecting group can be removed using a weak alkaline solution, e.g., 1,8-diazabicyclo[5,4,0]undec-7-ene(DBU) in acetonitrile, to expose the hydroxyl groups on the termini of the branches. Various functional groups X can be introduced onto the hydroxyl groups using different phosphoramidite modifiers (114). For example, the functional groups X can be: alkyne, azide or other suitable reactive pair member.

After the attachment of the phosporamidite modifiers with the functional groups, the CPG solid support bearing the branched entity (115) can be treated with concentrated ammonium hydroxide to remove the protecting groups and cleave the branched entity from the solid support. The desired full length branched product containing a trityl hydrophobic group can be isolated from the crude mixture using HPLC (High performance Liquid Chromatography). Afterwards, trityl group is removed by treating the purified product with acid. The disulfide bond can be reduced using a reducing reagent, such as DTT, to generate a thio group at the terminus of the branched linker (116). The branched linker (116) can be used for conjugation with biomolecules with affinity for the target molecules, such as oligonucleotides, peptides proteins, carbohydrates, lipids, etc.

Figure 14:
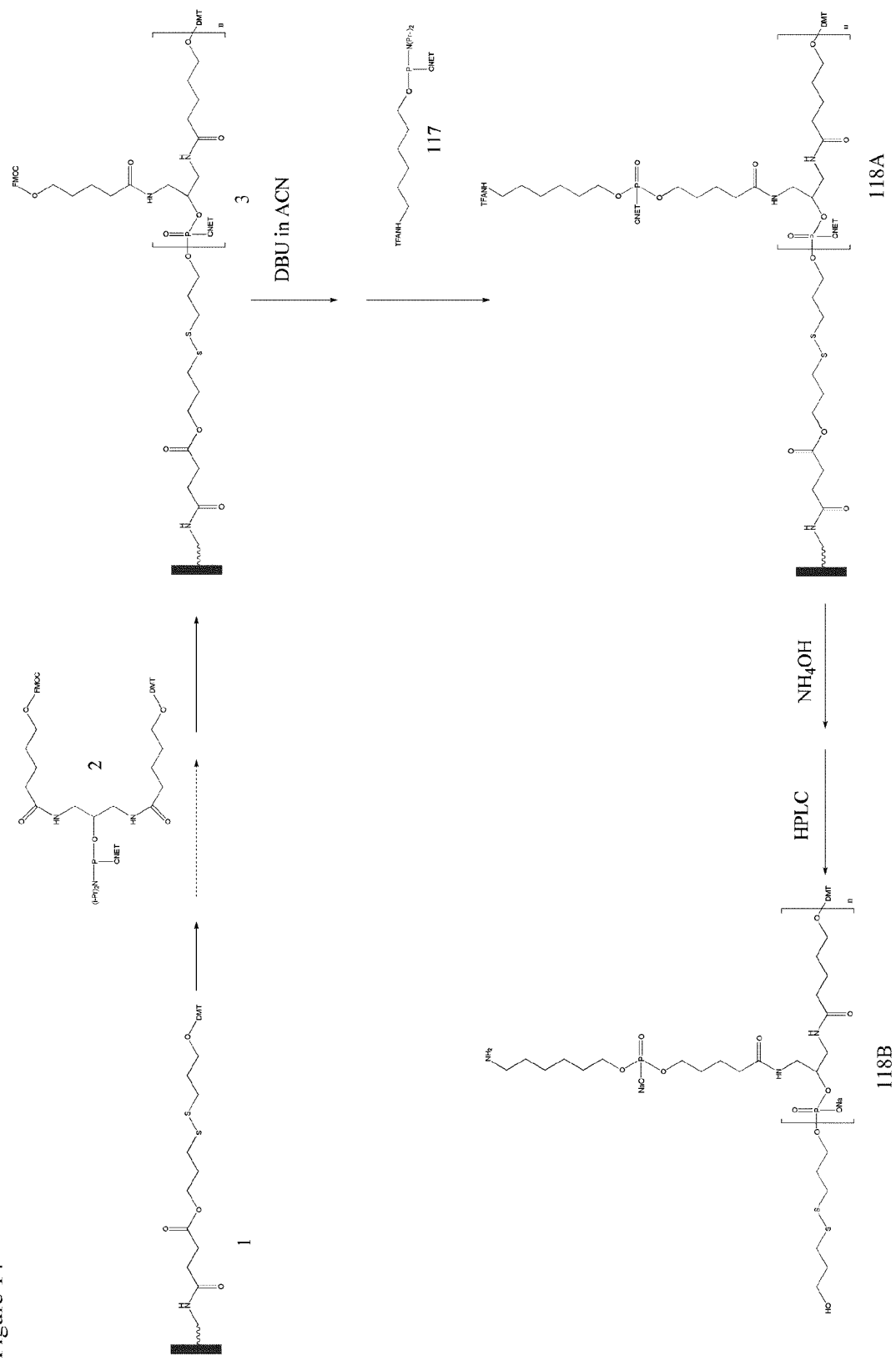
FIG. 14 illustrates a synthesis scheme for a branched moiety comprising multiple amino groups which can be converted to various first members of a reactive pair.

A method for introducing amino functional groups onto the side chains of the branched entities for conjugating with various biomolecules is shown in FIG. 14.

Using the phosphoramidite synthesis chemistry described above, one can incorporate a chosen number of units of "Y" shape bifunctional monomer (2) to form the branched entities (3) on the solid support. The FMOC protecting group can be removed with a weak alkaline solution, e.g., DBU in acetonitrile. On the exposed hydroxyl group, an amino modifier phosphoramidite monomer, such as 5'-Amino-Modifier C6-TFA (117) (from Glen research) can be coupled to produce molecule (118A). Then, the branched entity can be deprotected and cleaved from the solid support by treating it with concentrated ammonium hydroxide.

Figure 15:
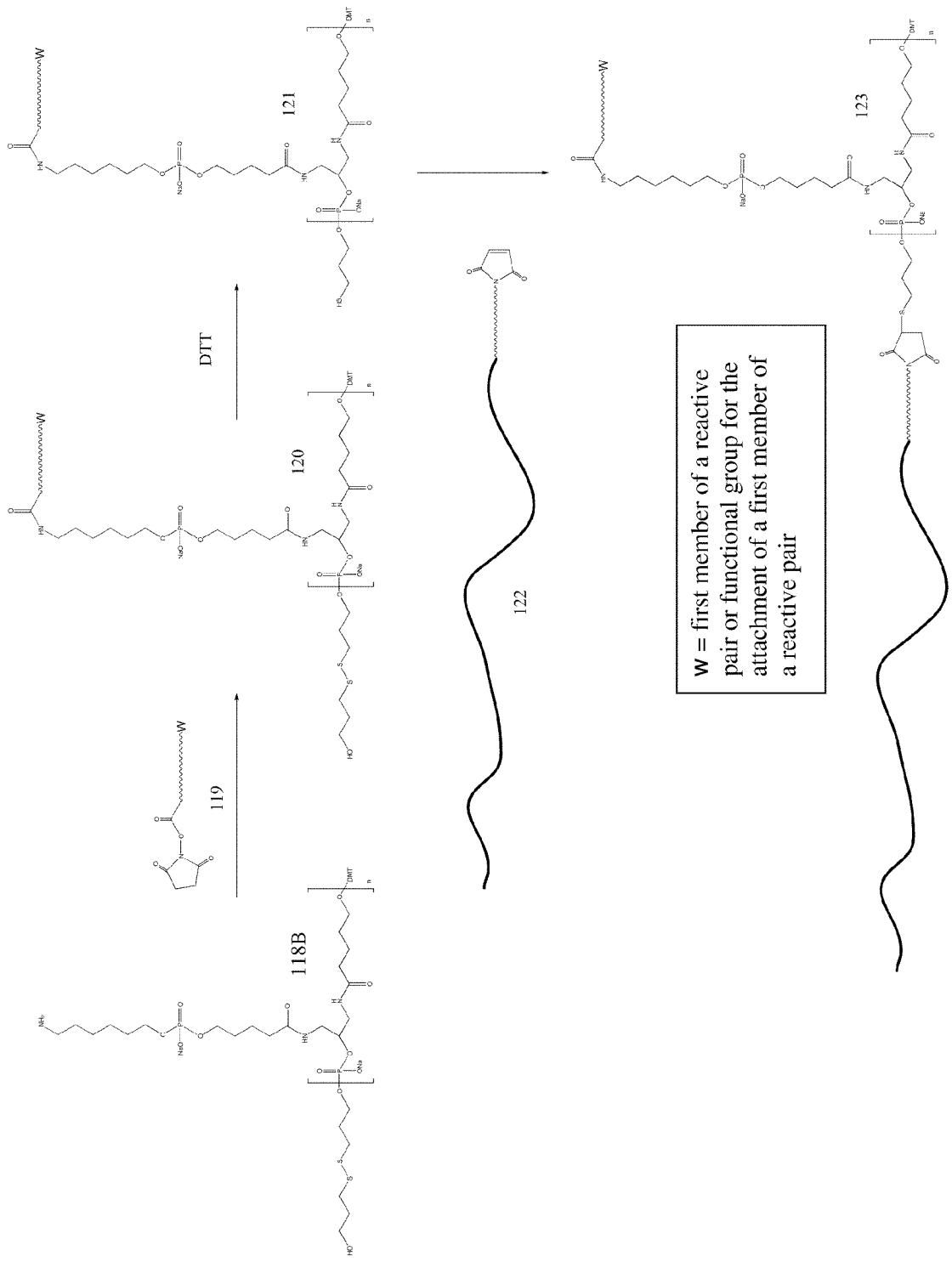
FIG. 15 illustrates a synthesis scheme using the branched moiety comprising multiple amino groups shown in FIG. 14 for the synthesis of a branched moiety comprising multiple first members of a reactive pair and its conjugation with a target-specific binding moiety.

After HPLC purification, the branched entity with amino groups on its side chains (118B) is ready for further conjugation. Many modification and cross linking reagents can be used. As shown in FIG. 15, a linking reagent (119) with N-hydroxysuccimide (NHS) ester at one terminus and a first member of a reactive pair (W), at the other terminus can be utilized. Linkers like (119) are available commercially or can be custom synthesized. Many biomolecules, such as carbohydrate, peptide, protein, DNA RNA, etc, can be chemically modified or conjugated with linkers to introduce the NHS ester group for reacting with the amino groups on the branched entity (118B).

After the formation of (120) by modifying the side chains of (118B) with (119), the disulfide bond in (120) can be converted to a free thio group in (121) by applying reduction reagent like DTT. Then, a maleimide functionalized biomolecules (122), e.g., an oligonucleotide, can be conjugated with thio on (121).

Example 4

"Direct" Synthesis Scheme for a Branched Linking Molecule

Figure 16:
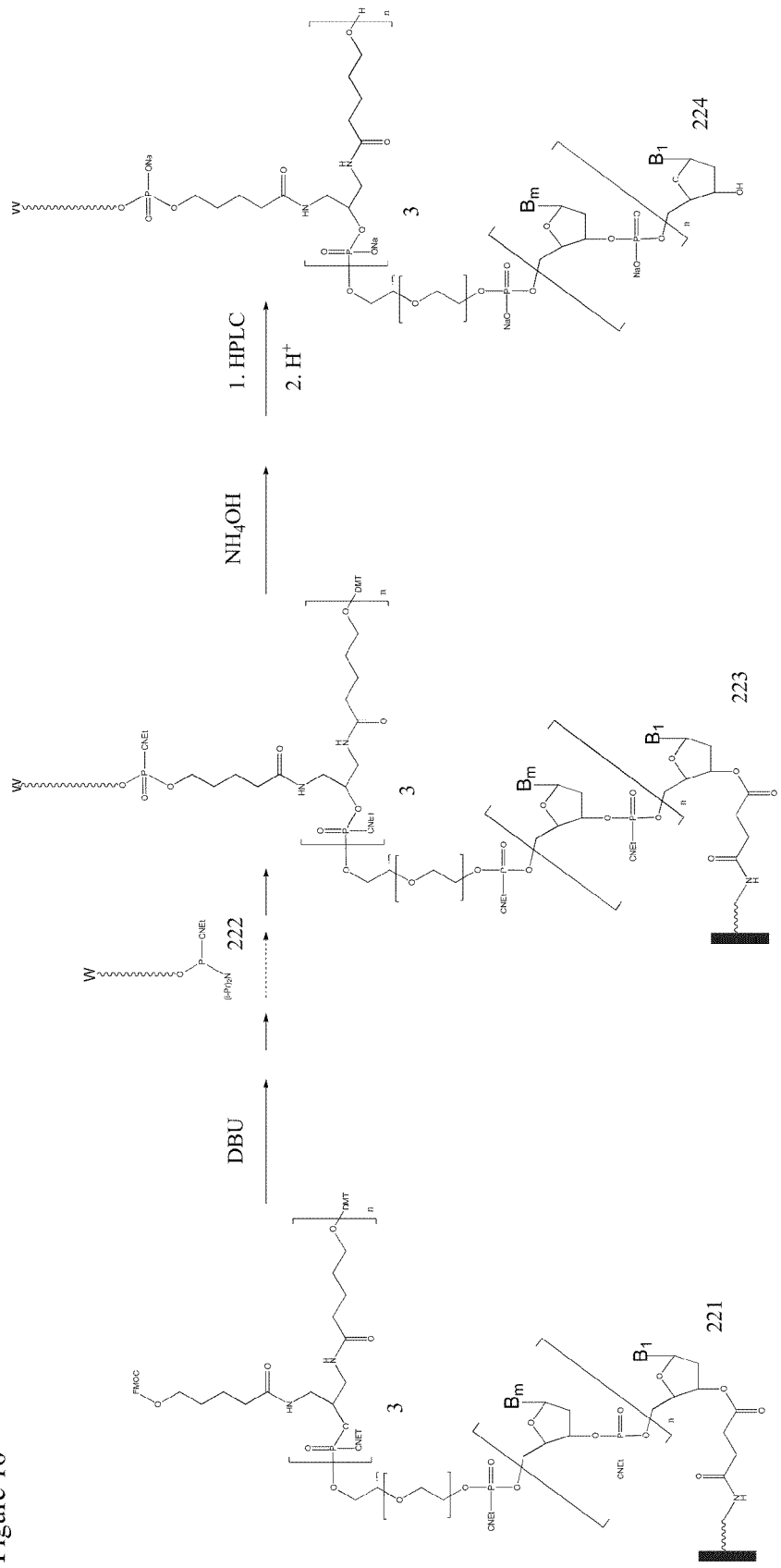
FIG. 16 illustrates a scheme for the direct synthesis of a branched linking molecule comprising an ODN target-specific binding moiety and multiple first members of a reactive pair.

Another approach, described in FIG. 16, is to synthesize and modify a branched linker at the 5'-terminal of an oligonucleotide on solid phase. Many functional groups and molecules can be linked on the side chains of the branched linker.

An oligonucleotide can be synthesized on a solid support using phosphoramidite synthesis chemistry. Optionally, a chemical spacer can be incorporated on the terminal of the oligoncleotide with spacers bearing phosphoramidite. Then, a branched entity can be synthesized directly onto the oligonucleotide or on the spacer, if present. After removing the DMT protecting group from the oligonucleotide or the spacer, a unit of "Y" shape bifunctional monomer (2) is coupled to the exposed hydroxyl group using phosphoramidite synthesis chemistry. The "Y" shape bifunctional monomer (2) has two different protecting groups at each terminal: DMT, an acid labile group, and FMOC, a base labile group. The DMT group is deblocked using acidic solution, and then another unit of the "Y" shape bifunctional monomer (2) is incorporated to extend the branch backbone. By repeating this process a pre-determined number of the "Y" shape bifunctional monomer (2) can be incorporated to form (221) with branched structure.

The FMOC protecting groups on the side chains of the branched entity can be removed using a weak base solution, e.g., DBU in acetonitrile, to expose the hydroxyl groups which can be modified to form many functional groups or conjugate with bio-molecules. These modifications can be introduced using suitable phosphoramidite modifiers (222). Functional groups and molecules used in the modification can include, e.g., alkyne, azide, or other suitable first member of a reactive pair.

The synthesized oligonucleotide and branched linker (223) bearing multiple functional groups or molecules on the side chains is deprotected and cleaved from the solid support by concentrated ammonium hydroxide. The ammonia is removed by evaporation. The desired branched linker product containing a trityl hydrophobic group is isolated from the crude mixture using HPLC. The trityl group is cleaved by treating with acid and can be removed by n-butanol extraction. The pure oligonucleotide and branched linker (224) bearing multiple functional groups or molecules on the side chains can be utilized for many applications, including but not limited to the cross-linking of a nucleic acid target molecule and a magnetic particle on a MTJ biosensor.

Example 5

Introducing Covalent Binding Interactions to Produce a Detectable Covalent Binding Complex Comprising a Nucleic Acid Target Molecule, a Biochip Surface and a Magnetic Particle In the following prophetic example, click chemistry is utilized to produce a robust covalently linked structure to enhance particle-based detection of nucleic acid target molecules. FIG. 5 shows the formation of a binding complex using a target-immobilization probe, a linking molecule and a magnetic particle to capture and label a target nucleic acid sequence.

A nucleic acid target molecule is hybridized with a target-immobilization probe on a biochip surface, followed by hybridization of a linking molecule The linking molecule comprises a first click chemistry functional group, denoted X, and a nucleic acid sequence capable of hybridizing specifically with the target molecule. A wash step can be performed to remove linking molecules not specifically hybridized to the target. The resulting non-covalent structure can then be cross-linked with a nucleic acid-cross linking agent, e.g., psoralen.

Subsequent to the psoralen cross-linking, the structure can be incubated with magnetic particles functionalized with a second click chemistry functional group (denoted Y) capable of reacting with the first click chemistry functional group to complete the covalent "fixing" of the nucleic acid detection structure between the biochip surface and the magnetic particle.

Where the reaction of the click chemistry functional groups requires the addition of a catalyst, e.g., in azide/alkyne [3+2] cycloaddition, a suitable catalyst (e.g., Cu ion) is included. Alternatively, reactions such as the azide/DIFO reaction may be utilized to covalently link the magnetic particle and the linking molecule in the absence of added Cu ion catalyst. The resulting covalent binding complex can be detected using a magnetic tunnel junction (MTJ) sensor.

In an additional example, the magnetic particle is functionalized with a click chemistry functional group, denoted Y. As shown in FIG. 6, a nucleic acid target molecule is amplified using PCR. In the reaction mixture, one or more of the standard deoxynucleotide triphosphates (dNTPs) are replaced with a dNTP modified to introduce a first click chemistry functional group. As a result, the amplicon has one or more bases modified to include the first click chemistry functional group, denoted X. The amplicon can be hybridized to a target-immobilization probe on the surface of a biochip. The target immobilization probe can also be modified to contain a second click chemistry functional group, denoted Y, which, under suitable conditions, is capable of forming a covalent bond with a first member of the reactive pair present in the amplicon.

The non-covalent structure formed via hybridization can be incubated with magnetic particles functionalized with second click chemistry functional groups, wherein the incubation is under conditions suitable for the formation of covalent bonds between the first and second click chemistry functional groups, e.g., the incubation can be designed to take place in the presence of a Cu ion catalyst.

Optionally, psorlan or another suitable nucleic acid cross-linking agent can be used to introduce covalent bonds between non-covalently bound members of the complex, thereby further stabilizing the detectable covalent binding complex.

A further example is illustrated in FIG. 7. In a first step, a nucleic acid target molecule is amplified using PCR. In the reaction mixture, one or more of the standard deoxynucleotide triphosphates (dNTPs) are replaced with a dNTP modified to introduce first click chemistry functional groups. As a result, the amplicon has one or more bases modified to include first click chemistry functional groups, denoted X. The amplicon can then be hybridized to a target-immobilization probe on the surface of a biochip. The target immobilization probe is modified to contain a second click chemistry functional group, denoted Y, which, under suitable conditions, is capable of forming a covalent bond with a first click chemistry functional group present in the amplicon.

The non-covalent structure formed via hybridization can then be incubated with magnetic particles functionalized with a labeling probe which comprises a nucleic acid sequence capable of hybridizing specifically with a sequence of the amplicon. The labeling probe also comprises a second click chemistry functional group, which, under suitable conditions, is capable of forming a covalent bond with a first member of the reactive pair in the amplicon. Hybridization of the labeling probe with the amplicon completes a non-covalent nucleic acid binding complex. Where the covalent bond forming reaction requires the addition of Cu catalyst, such a catalyst is added.

The resulting covalent bonds "fix" the nucleic acid detection structure between the biochip surface and the magnetic particle thereby producing a detectable covalent binding complex. The resulting covalent binding complex can be detected using a magnetic sensor, e.g., an MTJ sensor.

Optionally, psorlan or another suitable nucleic acid cross-linking agent can be used to introduce covalent bonds between non-covalently bound members of the complex, thereby further stabilizing the detectable covalent binding complex.

Exemplary covalent bond forming conditions are as follows: in the presence of
Copper (I) catalyst, 1,3-cycloaddition occurs between the alkyne and azide groups to form a triazole bond—a covalent link. Typical click chemistry reaction conditions are either phosphate buffered saline, pH 7.4-0.1% Tween or a tertiary butanol—water mixture containing 0.1 mM Copper Sulfate and 1 mM reducing agent (e.g. Sodium Ascorbate or Tris (2-carboxyethyl)phosphine (TCEP)) to reduce the Copper (II) to an active Copper (I) species. Copper (I) stabilizing ligands such as Tris[(1-benzyl-1H-1,2,3-triazol-4-yl) methyl] amine (TBTA) can also be used to increase the efficiency and rate of reaction, usually in 2-5 fold molar excess of the Cu (I) species. If appropriate and compatible with the biomolecular non-covalent complex, click chemistry reactions are efficiently performed in polar solvents such as acetonitrile or dimethylformamide using Copper(I) Iodide as the source for an active Cu(I) species.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of generating a covalent binding complex comprising a target molecule, said method comprising:
   combining in a reaction mixture
   a substrate surface, wherein said substrate surface comprises a plurality of target-immobilization probes,
   a detectable label, wherein said detectable label comprises a plurality of first members of a reactive pair;
   a sample suspected of containing a target molecule; and
   a linking molecule, wherein said linking molecule comprises
   a plurality of target-specific binding moieties which specifically bind to said target molecule, when present, wherein each of said target-specific binding moieties specifically binds to a different region of said target molecule when present; and
   a plurality of second members of said reactive pair,
   wherein said combining is under reaction conditions sufficient to provide for specific binding of said target molecule, if present, to one of said plurality of target-immobilization probes, and
   wherein said combining is under reaction conditions sufficient to provide for specific binding of said linking molecule to said target molecule, if present; and
   subjecting said reaction mixture to conditions suitable for formation of a plurality of covalent bonds between members of said plurality of first members of said reactive pair and members of said plurality of second members of said reactive pair, wherein, when said target molecule is present in said sample, one of said plurality of target-immobilization probes specifically binds to said target molecule, said linking molecule specifically binds to said target molecule and forms a plurality of covalent bonds via reaction of said members of said plurality of first members with said members of said plurality of second members of said reactive pair, thereby forming a complex comprising said substrate surface, said one of said plurality of target-immobilization probes, said target molecule, said linking molecule and said detectable label, and wherein said detectable label is a particle having a diameter of from 0.2 μm to 5 μm and said complex does not comprise more than one of said particle.

2. A method of generating a covalent binding complex comprising a target molecule, said method comprising:
   combining in a reaction mixture
   a substrate surface, wherein said substrate surface comprises a plurality of target immobilization probes;
   a detectable label, wherein said detectable label comprises a plurality of first members of a reactive pair;
   a sample suspected of containing a target molecule; and
   a plurality of linking molecules, wherein each member of said plurality of linking molecules is independently present in one or more copies, and wherein each member comprises
   a target-specific binding moiety which specifically binds to a different region of said target molecule relative to the target-specific binding moieties of the other members of the plurality of linking molecules, when present; and
   a second member of said reactive pair,
   wherein said combining is under reaction conditions sufficient to provide for specific binding of said target molecule, if present, to one of said plurality of target-immobilization probes, and
   wherein said combining is under reaction conditions sufficient to provide for specific binding of said plurality of linking molecules to said target molecule, if present; and
   subjecting said reaction mixture to conditions suitable for formation of covalent bonds between first members of said reactive pair and second members of said reactive pair, wherein, when said target molecule is present in said sample, one of said plurality of target-immobilization probes specifically binds to said target molecule, said plurality of linking molecules specifically binds to a plurality of different regions of said target molecule and forms a plurality of covalent bonds via reaction of the first members of said reactive pair with the second members of said reactive pair, thereby forming a complex comprising said substrate surface, said one of said plurality of target immobilization probes, said target molecule, said plurality of linking molecules and said detectable label, and wherein said detectable label is a particle having a diameter of from 0.2 µm to 5 µm and said complex does not comprise more than one of said particle.

3. A reaction mixture comprising:
a substrate surface, wherein said substrate surface comprises a plurality of target-immobilization probes;
a detectable particle having a diameter of from 0.2 µm to 5 µm, wherein said detectable particle comprises a plurality of first members of an azide/alkyne reactive pair;
a sample suspected of containing a target molecule; and
a linking molecule, wherein said linking molecule comprises
  a plurality of target-specific binding moieties which specifically bind to said target molecule, when present, wherein each of said target-specific binding moieties specifically binds to a different region of said target molecule when present; and
  a plurality of second members of said azide/alkyne reactive pair,
wherein when said target molecule is present in said sample, one of said plurality of target-immobilization probes specifically binds to said target molecule, said linking molecule specifically binds to said target molecule and forms a plurality of covalent bonds via reaction of members of said plurality of first members with members of said plurality of second members of said azide/alkyne reactive pair, thereby forming a complex comprising said substrate surface, said one of said plurality of target-immobilization probes, said target molecule, said linking molecule and said detectable particle, and wherein said complex does not comprise more than one of said detectable particle.

4. The reaction mixture of claim 3, wherein said detectable particle is a magnetic particle.

5. A reaction mixture comprising:
a substrate surface, wherein said substrate surface comprises a plurality of target-immobilization probes;
a detectable particle having a diameter of from 0.2 µm to 5 µm, wherein said detectable particle comprises a plurality of first members of a reactive pair;
a sample suspected of containing a target molecule; and
a plurality of linking molecules, wherein each member of said plurality of linking molecules is independently present in one or more copies, and wherein each member comprises
  a target-specific binding moiety which specifically binds to a different region of said target molecule relative to the target-specific binding moieties of the other members of the plurality of linking molecules, when present; and
  a second member of said reactive pair,
wherein when said target molecule is present in said sample, one of said plurality of target-immobilization probes specifically binds to said target molecule, said plurality of linking molecules specifically binds to a plurality of different regions of said target molecule and forms a plurality of covalent bonds via reaction of first members of said reactive pair with second members of said reactive pair, thereby forming a complex comprising said substrate surface, said one of said plurality of target-immobilization probes, said target molecule, said plurality of linking molecules, and said detectable particle, and wherein said complex does not comprise more than one of said detectable particle.

6. The reaction mixture of claim 5, wherein said detectable particle is a magnetic particle.

7. The method of claim 1, wherein said detectable label is a magnetic particle.

8. The method of claim 1, wherein said target molecule is a nucleic acid target molecule.

9. The method of claim 1, wherein said method further comprises detecting the presence, absence and/or amount of said covalent binding complex.

10. The method of claim 1, wherein said reactive pair is an azide/alkyne reactive pair.

11. The method of claim 2, wherein said detectable label is a magnetic particle.

12. The method of claim 2, wherein said target molecule is a nucleic acid target molecule.

13. The method of claim 2, wherein said method further comprises detecting the presence, absence and/or amount of said covalent binding complex.

14. The method of claim 2, wherein said reactive pair is an azide/alkyne reactive pair.

15. The reaction mixture of claim 3, wherein said target molecule is a nucleic acid target molecule.

16. The reaction mixture of claim 5, wherein said target molecule is a nucleic acid target molecule.

17. The reaction mixture of claim 5, wherein said reactive pair is an azide/alkyne reactive pair.

* * * * *